(12) United States Patent
Hess et al.

(10) Patent No.: US 11,047,865 B2
(45) Date of Patent: Jun. 29, 2021

(54) TROPONIN AND BNP BASED DIAGNOSIS OF RISK PATIENTS AND CAUSE OF STROKE

(71) Applicant: Roche Diagnostics Operations, Inc., Indianapolis, IN (US)

(72) Inventors: Georg Hess, Mainz (DE); Andrea Horsch, Lucerne (CH); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/911,695

(22) Filed: Mar. 5, 2018

(65) Prior Publication Data

US 2018/0196066 A1    Jul. 12, 2018

Related U.S. Application Data

(63) Continuation of application No. 15/285,798, filed on Oct. 5, 2016, now abandoned, which is a continuation of application No. 14/859,616, filed on Sep. 21, 2015, now abandoned, which is a continuation of application No. 14/251,803, filed on Apr. 14, 2014, now abandoned, which is a continuation of application No. PCT/EP2012/070553, filed on Oct. 17, 2012.

(30) Foreign Application Priority Data

Oct. 17, 2011  (EP) .................................... 11185421

(51) Int. Cl.
*G01N 33/53* (2006.01)
*G01N 33/68* (2006.01)
*G01N 33/543* (2006.01)

(52) U.S. Cl.
CPC ... *G01N 33/6887* (2013.01); *G01N 33/54306* (2013.01); *G01N 33/6893* (2013.01); *G01N 2333/47* (2013.01); *G01N 2333/4712* (2013.01); *G01N 2800/326* (2013.01)

(58) Field of Classification Search
None
See application file for complete search history.

(56) References Cited

U.S. PATENT DOCUMENTS

| | | | |
|---|---|---|---|
| 5,744,305 A | 4/1998 | Fodor et al. |
| 6,331,402 B1 | 12/2001 | Nussbaum et al. |
| 6,709,855 B1 | 3/2004 | Stanton et al. |
| 6,974,704 B2 | 12/2005 | Nelson et al. |
| 8,354,235 B2 | 1/2013 | Bodenbach et al. |
| 2003/0039584 A1 | 2/2003 | Schabbach et al. |
| 2003/0232385 A1 | 12/2003 | Breit et al. |
| 2006/0003338 A1 | 1/2006 | Deng et al. |
| 2009/0176247 A1 | 7/2009 | Bashirians et al. |
| 2009/0233312 A1 | 9/2009 | Gibbons et al. |
| 2010/0197518 A1 | 8/2010 | Xu et al. |
| 2010/0285491 A1 | 11/2010 | Wienhues-Thelen et al. |
| 2011/0111524 A1 | 5/2011 | Goix et al. |

FOREIGN PATENT DOCUMENTS

| | | |
|---|---|---|
| CN | 101107527 A | 1/2008 |
| CN | 101379401 A | 3/2009 |
| CN | 101393198 A | 3/2009 |
| CN | 101501067 A | 8/2009 |
| CN | 101506660 A | 8/2009 |
| EP | 0648228 B1 | 11/1998 |
| EP | 1577673 A1 | 9/2005 |
| EP | 2037278 A1 | 3/2009 |
| WO | 1999/006445 A1 | 2/1999 |
| WO | 2000/070051 A1 | 11/2000 |
| WO | 2002/083913 A1 | 10/2002 |
| WO | 2002/089657 A2 | 11/2002 |
| WO | 2003/016910 A1 | 2/2003 |
| WO | 2003/025571 A1 | 3/2003 |
| WO | 2004/059293 A2 | 7/2004 |
| WO | 2005/113585 A2 | 12/2005 |
| WO | 2006/087373 A1 | 8/2006 |
| WO | 2006/131529 A1 | 12/2006 |
| WO | 2007/090796 A1 | 8/2007 |
| WO | 2007/137865 A1 | 12/2007 |
| WO | 2008/015254 A2 | 2/2008 |
| WO | 2008/068780 A2 | 6/2008 |
| WO | 2009/047283 A2 | 4/2009 |
| WO | 2009/047285 A1 | 4/2009 |
| WO | 2010/007041 A1 | 1/2010 |
| WO | 2010/017972 A1 | 2/2010 |
| WO | 2010/046136 A1 | 4/2010 |
| WO | 2010/124821 A1 | 11/2010 |

(Continued)

OTHER PUBLICATIONS

Van Der Vekens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Abdollahi, Amir et al., Endostatin's Antiangiogenic Signaling Network, Molecular Cell, 2004, pp. 649-663, vol. 13.
Adams, Harold P., Jr. et al., Classification of subtype of acute ischemic stroke. Definitions for use in a multicenter clinical trial. TOAST. Trial of Org 10172 in Acute Stroke Treatment., Stroke, 1993, pp. 35-41, vol. 24.

(Continued)

*Primary Examiner* — Gary Counts
(74) *Attorney, Agent, or Firm* — Stinson LLP

(57) ABSTRACT

Method for determination of whether a subject suffers from intermittent atrial fibrillation based on the determination of the amount of a Troponin T in a sample in a patient suffering from atrial fibrillation using a binding assay. Kits and devices adapted to carry out the methods are also provided.

14 Claims, No Drawings

(56) References Cited

FOREIGN PATENT DOCUMENTS

| WO | 2011/012268 A1 | 2/2011 |
|---|---|---|
| WO | 2012/025355 A1 | 3/2012 |
| WO | 2014/040759 A1 | 3/2014 |
| WO | 2014/072471 A1 | 5/2014 |
| WO | 2014/086833 A1 | 6/2014 |

OTHER PUBLICATIONS

Adams, Harold P., Jr. et al., Guidelines for the Early Management of Adults With Ischemic Stroke, Stroke, 2007, pp. 1655-1711, vol. 38.
Agewall, S. et al., Troponin elevation in coronary vs. non-coronary disease, European Heart Journal, 2011, pp. 404-411, vol. 32.
Alcaraz, Raul and Rieta, Jose Joaquin, Sample entropy of the main atrial wave predicts spontaneous termination of paroxysmal atrial fibrillation, Medical Engineering & Physics, 2009, pp. 917-922, vol. 31.
Anderson, Jeffrey L. et al., ACC/AHA 2007 Guidelines for the Management of Patients With Unstable Angina/Non-ST-Elevation Myocardial Infarction, Journal of the American College of Cardiology, 2007, pp. e1-e157, vol. 50, No. 7.
Anderson, Page A. W. et al., Molecular Basis of Human Cardiac Troponin T Isoforms Expressed in the Developing, Adult, and Failing Heart, Circulation Research, 1995, pp. 681-686, vol. 76.
Baek, Seung Joon et al., Cyclooxygenase Inhibitors Regulate the Expression of a TGF-β Superfamily Member That Has Proapoptotic and Antitumorigenic Activities, Molecular Pharmacology, 2001, pp. 901-908, vol. 59, No. 4.
Bauskin, Asne R. et al., The propeptide of macrophage inhibitory cytokine (MIC-1), a TGF-β superfamily member, acts as a quality control determinant for correctly folded MIC-1, The EMBO Journal, 2000, pp. 2212-2220, vol. 19, No. 10.
Beaulieu-Boire, Isabelle et al., Troponin Elevation Predicts Atrial Fibrillation in Patients with Stroke or Transient Ischemic Attach, Journal of Stroke and Cerebrovascular Diseases, 2013, pp. 978-983, vol. 22, No. 7.
Beck-Da-Silva, Luis et al., Brain natriuretic peptide predicts successful cardioversion in patients with atrial fibrillation and maintenance of sinus rhythm, Canadian Journal of Cardiology, 2004, pp. 1245-1248, vol. 20, No. 12.
Becker, Richard C., Biomarkers in Atrial Fibrillation: Investigating Biologic Plausibility, Cause, and Effect, Journal of Thrombosis and Thrombolysis, 2005, pp. 71-75, vol. 19, No. 1.
Boehm, Michael et al., Biomarkers: optimizing treatment guidance in heart failure, Clinical Research in Cardiology, 2011, pp. 973-981, vol. 100.
Bonow, Robert O., New Insights Into the Cardiac Natriuretic Peptides, Circulation, 1996, pp. 1946-1950, vol. 93.
Bootcov, Michelle R. et al., MIC-1, a novel macrophase inhibitory cytokine, is a divergent member of the TGF-β superfamily, Proceedings of the National Academy of Sciences USA, 1997, pp. 11514-11519, vol. 94.
Brown, David A. et al., Concentration in plasma of macrophage inhibitory cytokine-1 and risk of cardiovascular events in women: a nested case-control study, Lancet, 2002, pp. 2159-2163, vol. 359.
Brugts, Jasper J. et al., The predictive value of cardiac biomarkers in prognosis and risk stratification of patients with atrial fibrillation, Current Opinion in Cardiology, 2011, pp. 449-456, vol. 26.
Burnicourt, Jean-Marc et al., Troponin Levels Help Predict New-Onset Atrial Fibrillation in Ischaemic Stroke Patients: A Retrospective Study, European Neurology, 2009, pp. 24-28, vol. 63.
Böttner, Martina et al., Characterization of the rat, mouse, and human genes of growth/differentiation factor-15/macrophage inhibiting cytokine-1 (GDF-15/MIC-1), Gene, 1999, pp. 105-111, vol. 237.
Cheng, Tao et al., Correlation between atrial fibrillation, serum amyloid protein A and other inflammatory cytokines, Molecular Medicine Reports, 2012, pp. 581-584, vol. 6.
Choudhury, Anirban et al., Soluble CD40 Ligand, Platelet Surface CD40 Ligand, and Total Platelet CD40 Ligand in Atrial Fibrillation, Chest, 2008, pp. 574-581, vol. 134.
Cohen, Ariel et al., D-dimers in atrial fibrillation: a further step in risk stratification of thrombo-embolism?, European Heart Journal, 2007, pp. 2179-2180, vol. 28.
De Filippi, Christopher R. et al., Clinical Validation of a Novel Assay for Galectin-3 for Risk Assessment in Acutely Destabilized Heart Failure, The 13th Annual Scientific Meeting HFSA, 2009, p. S9, Abstract 020.
Dickstein, Kenneth et al., ESC Guidelines for the diagnosis and treatment of acute and chronic heart failure 2008, European Heart Journal, 2008, pp. 2388-2442, vol. 29.
Dieplinger, Benjamin et al., Long-term stability of soluble ST2 in frozen plasma samples, Clinical Biochemistry, 2010, pp. 1169-1170, vol. 43.
Donnan, Geoffrey et al., Stroke, Lancet, 2008, pp. 1612-1623, vol. 371.
Dou, Chunyan et al., Nephrotoxic effect of melamine-contaminated fodder on rat: a metabonomic study, Chinese Journal of Pharmacology & Toxicology, 2011, pp. 88-92, vol. 25, No. 1.
European Search Report dated Sep. 20, 2016 in Application No. 16175468.4-1405, 12 pages.
Ferrieres, Gaelle et al., Human cardiac troponin I: precise identification of antigenic epitopes and prediction of secondary structure, Clinical Chemistry, 1998, pp. 487-493, vol. 44, No. 3.
Finsterer, J. et al., Positive troponin-T in noncompaction is associated with neuromuscular disorders and poor outcome, Clinical Research in Cardiology, 2007, pp. 109-113, vol. 96.
Fonarow, Gregg C. et al., Usefulness of B-Type Natriuretic Peptide and Cardiac Troponin Levels to Predict In-Hospital Mortality from ADHERE, American Journal of Cardiology, 2008, pp. 231-237, vol. 101.
Foreman, J. H. et al., Cardiac Troponin-1 Plasma Concentration in Normal Horses and in Horses with Arrhythmias and Toxicities, ACVIM Abstracts, 2005, p. 478, Abstract No. 286.
Fuster, Valentin et al., ACC/AHA/ESC Guidelines for the Management of Patients With Atrial Fibrillation: Executive Summary, Circulation, 2001, pp. 2118-2150, vol. 104.
Garcia-Berrocosco, Teresa et al., Blood Biomarkers in Cardioembolic Stroke, Current Cardiology Reviews, 2010, pp. 194-201, vol. 6.
Gardner, R. S. et al., N-terminal pro-brain natriuretic peptide A new gold standard in predicting mortality in patients with advanced heart failure, European Heart Journal, 2003, pp. 1735-1743, vol. 24.
Goei, Dustin et al., Influence of Renal Function on the Usefulness of N-Terminal Pro-B-Type Natriuretic Peptide as a Prognostic Cardiac Risk Marker in Patients Undergoing Noncardiac Vascular Surgery, American Journal of Cardiology, 2008, pp. 122-126, vol. 101.
Goette, Andreas et al., Acute atrial tachyarrhytmia induces angiotensin II type 1 receptor-mediated oxidative stress and micovascular flow abnormalities in the ventricles, European Heart Journal, 2009, pp. 1411-1420, vol. 30, No. 11.
Grigoryan, S. V. and Hazarapetyan, L. G., Impact of Inflammatory Markers on Pathogenesis and Clinical Outcomes at Different Types of Atrial Fibrillation, 2013, pp. 4-8, vol. 7, No. 3.
Gustafsson, Finn et al., Diagnostic and Prognostic Performance of N-Terminal ProBNP in Primary Care Patients With Suspected Heart Failure, Journal of Cardiac Failure, 2005, pp. S15-S20, vol. 11, No. 5, Supplement.
Heeringa, Jan et al., Prevalence, incidence and lifetime risk of atrial fibrillation: the Rotterdam study, European Heart Journal, 2006, pp. 949-953, vol. 27.
Hijazi, Z. et al., Troponin 1 elevation increases the risk of death and stroke in patients with atrial fibrillation, European Heart Journal, 2010, p. 886, vol. 31, Supplement 1.
Hijzai, Ziad et al., Cardiac Biomarkers Are Associated With an Increased Risk of Stroke and Death in Patients With Atrial Fibrillation A Randomized Evaluation of Long-Term Anticoagulation Therapy (RE-LY) Substudy, Circulation, 2012, pp. 1605-1616, vol. 125.
Hromas, Robert et al., PLAB, a novel placental bone morphogenetic protein, Biochimica et Biophysica Acta, 1997, pp. 40-44, vol. 1354.

(56) References Cited

OTHER PUBLICATIONS

Hunt, Sharon A. et al., ACC/AHA Guidelines for the Evaluation and Management of Chronic Heart Failure in the Adult: Executive Summary, Journal of the American College of Cardiology, 2001, pp. 2101-2113, vol. 38, No. 7.

Hunt, Sharon Ann et al., ACC/AHA 2005 Guideline Update for the Diagnosis and Management of Chronic Heart Failure in the Adult, Journal of the American College of Cardiology, 2005, pp. e1-e82, vol. 46.

Hwa, Vivian et al., The Insulin-Like Growth Factor-Binding Protein (IGFBP) Superfamily, Endocrine Reviews, 1999, pp. 761-787, vol. 20, No. 6.

International Search Report dated Apr. 11, 2013, in Application No. PCT/EP20121070553, 6 pages.

Irby, R. B. et al., Osteopontin regulates multiple functions contributing to human colon cancer development and progression, Clinical & Experimental Metastasis, 2004, pp. 515-523, vol. 21.

Jones, John I. and Clemmons, David R., Insulin-Like Growth Factors and Their Binding Proteins: Biological Actions, Endocrine Reviews, 1995, pp. 3-34, vol. 16, No. 1.

Juurlink, David N. et al., Rates of Hyperkalemia after Publication of the Randomized Aldactone Evaluation Study, The New England Journal of Medicine, 2004, pp. 543-551, vol. 351.

Kamel, Hooman and Smith, Wade S., Detection of Atrial Fibrillation and Secondary Stroke Prevention Using Telemetry and Ambulatory Cardiac Monitoring, Current Atherosclerosis Reports, 2011, pp. 338-343, vol. 13.

Karl, J. et al., Development of a novel, N-Terminal-proBNP (NT-proBNP) assay with a low detection limit, Scandinavian Journal of Clinical & Laboratory Investigation Supplement, 1999, pp. 177-181, vol. 59, Supplement 230.

Ke, Lei et al., Calpain mediates cardiac troponin degradation and contractile dysfunction in artrial fibrillation, Journal of Molecular and Cellular Cardiology, 2008, pp. 685-693, vol. 45.

Kempf, Tibor et al., Circulating Concentrations of Growth-Differentiation Factor 15 in Apparently Healthy Elderly Individuals and Patients with Chronic Heart Failure as Assessed by a New Immunoradiometric Sandwich Assay, Clinical Chemistry, 2007, pp. 284-291, vol. 53, No. 2.

Kempf, Tibor et al., Prognostic Utility of Growth Differentiation Factor-15 in Patients With Chronic Heart Failure, Journal of the American College of Cardiology, 2007, pp. 1054-1060, vol. 50, No. 11.

Kempf, Tibor et al., The Transforming Growth Factor-β Superfamily Member Growth-Differentiation Factor-15 Protects the Heart From Ischemia/Reperfusion Injury, Circulation Research, 2006, pp. 351-360, vol. 98.

Kerr, Gillian et al., Elevated Troponin after Stroke: A Systematic Review, Cerebrovascular Diseases, 2009, pp. 220-226, vol. 28.

Kirchhof, Paulus et al., Comprehensive risk reduction in patients with atrial fibrillation: Emerging diagnostic and therapeutic options, Thrombosis and Haemostasis, 2011, pp. 1012-1019, vol. 106, No. 6.

Kirchhof, Paulus et al., Comprehensive risk reduction in patients with atrial fibrillation: emerging diagnostic and therapeutic options—a report from the 3rd Atrial Fibrillation Competence NETwork/European Heart Rhythm Association consensus conference, Europace, 2012, pp. 8-27, vol. 14.

Kubo, Tow et al., Combined Measurements of Cardiac Troponin I and Brain Natriuretic Peptide Are Useful for Predicting Adverse Outcomes in Hypertrophic Cardiomyopathy, Circulation Journal, 2011, pp. 919-926, vol. 75.

Latini, R. et al., Circulating cardiovascular biomarkers in recurrent atrial fibrillation: data from the GISSI-Atrial Fibrillation Trial, Journal of Internal Medicine, 2011, pp. 160-171, vol. 269.

Lawton, Lee N. et al., Identification of a novel member of the TGF-beta superfamily highly expressed in human placenta, Gene, 1997, pp. 17-26, vol. 203.

Li, Jingtian and Wong, Lexin, B-type natriuretic peptide levels in patients with paroxysmal lone atrial fibrillation, Heart Vessels, 2006, pp. 137-140, vol. 21.

López-Bermejo, Abel et al., Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues, The Journal of Clinical Endocrinology & Metabolism, 2003, pp. 3401-3408, vol. 88, No. 7.

López-Bermejo, Abel et al., Insulin Resistance is Associated With Increased Serum Concentration of IGF-Binding Protein-Related Protein 1 (IGFBP-rP1/MAC25), Diabetes, 2006, pp. 2333-2339, vol. 55.

Maglione, Domenico et al., Two alternative mRNAs coding for the angiogenic factor, placenta growth factor (PlGF), are transcribed from a single gene of chromosome 14, Oncogene, 1993, pp. 2333-2339, vol. 8.

Masson, Serge et al., An Update on Cardiac Troponins as Circulating Biomarkers in Heart Failure, Current Heart Failure Reports, 2010, pp. 15-21, vol. 7.

Masson, Serge et al., Predicting atrial fibrillation recurrence with circulating inflammatory markers in patients in sinus rhythm at high risk for atrial fibrillation: data from the GISSI atrial fibrillation trial, Heart, 2010, pp. 1909-1914, vol. 96.

Mentz, Robert J. and Felker, G. Michael, Natriuretic Peptide-Guided Therapy for Heart Failure, 2011, pp. 2031-2037, vol. 75.

Morrish, D. W. et al., Identification by Subtractive Hybridization of a Spectrum of Novel and Unexpected Genes Associated with In Vitro Differentiation of Human Cytotrophoblast Cells, Placenta, 1996, pp. 431-441, vol. 17.

Moses, Marsha A. et al., Troponin I is present in human cartilage and inhibits angiogenesis, Proceedings of the National Academy of Sciences USA, 1999, pp. 2645-2650, vol. 96.

Mueller, Thomas et al., Comparison of the Biomedica NT-proBNP Enzyme Immunoassay and the Roche NT-proBNP Chemiluminescence Immunoassay: Implications for the Prediction of Symptomatic and Asymptomatic Structural Heart Disease, Clinical Chemistry, 2003, pp. 976-979, vol. 49, No. 6.

Nolan, John P. and Sklar, Larry A., Suspension array technology: evolution of the flat-array paradigm, TRENDS in Biotechnology, 2002, pp. 9-12, vol. 20, No. 1.

O'Donoghue, Michelle and Braunwald, Eugene, Natriuretic peptides in heart failure: should therapy be guided by BNP levels?, Nature Reviews Cardiology, 2010, pp. 13-20, vol. 7.

O'Reilly, Michael S. et al., Endostatin: An Endogenous Inhibitor of Angiogenesis and Tumor Growth, Cell, 197, pp. 277-285, vol. 88, 1997.

Oh, Youngman et al., Synthesis and Characterization of Insulin-like Growth Factor-binding Protein (IGFBP)-7, The Journal of Biological Chemistry, 1996, pp. 30322-30325, vol. 271, No. 48.

Omland, Torbjørn et al., A Sensitive Cardiac Troponin T Assay in Stable Coronary Artery Disease, The New England Journal of Medicine, 2009, pp. 2538-2547, vol. 361, No. 26.

Ortega, Nathalie and Werb, Zena, New functional roles for non-collagenous domains of basement membrane collagens, Journal of Cell Science, 2002, pp. 4201-4214, vol. 115.

Paralkar, Vishwas M. et al., Cloning and Characterization of a Novel Member of the Transforming Growth Factor-β/ Bone Morphogenetic Protein Family, The Journal of Biological Chemistry, 1998, pp. 13760-13767, vol. 273, No. 22.

Patel, Manesh R. et al., Rivaroxaban versus Warfarin in Nonvalvular Atrial Fibrillation, The New England Journal of Medicine, 2011, pp. 883-891, vol. 365, No. 10.

Pearson, Thomas A. et al., Markers of Inflammation and Cardiovascular Disease Application to Clinical and Public Health Practice A Statement for Healthcare Professionals From the Centers for Disease Control and Prevention and the American Heart Association, Circulation, 2003, pp. 499-511, vol. 107.

Petretto, Enrico et al., Integrated genomic approaches implicate osteoglycin (Ogn) in the regulation of left ventricular mass, Nature Genetics, 2008, pp. 546-552, vol. 40, No. 5.

Rizos J Human Hypertension 2010 24 447 457, Hypertension and paroxysmal atrial fibrillation: a novel predictive role of high sensitivity C-reactive protein in cardioversion and long-term recurrence, Journal of Human Hypertension, 2010, pp. 447-457, vol. 24.

(56) References Cited

OTHER PUBLICATIONS

Rizos, T. et al., Paroxysmal Atrial Fibrillation is More Prevalent than Persistent Atrial Fibrillation in Acute Stroke and Transient Ischemic Attach Patients, 2011, pp. 276-282, vol. 32.

Rodriquez-Yáñez, Manuel et al., High serum levels of pro-brain natriuretic peptide (pro BNP) identify cardioembolic origin in undetermined stroke, Disease Markers, 2009, pp. 189-195, vol. 26.

Sadanaga, Tsuneaki et al., D-dimer levels positively correlate with B-type natriuretic peptide levels in patients with atrial fibrillation, International Journal of Cardiology, 2012, pp. 110-111.

Sata, Naoyuki et al., C-reactive Protein and Atrial Fibrillation is inflammation a consequence or a cause of atrial fibrillation?, Japanese Heart Journal, 2004, pp. 441-445, vol. 45.

Schaeffer, Evelyne et al., Complete structure of the human transferrin gene. Comparison with analogous chicken gene and human pseudogene, Gene, 1987, pp. 109-116, vol. 56.

Schou, Morten et al., Long-term clinical variation of NT-proBNP in stable chronic heart failure patients, European Heart Journal, 2007, pp. 177-182, vol. 28.

Schou, Morten et al., Unexplained week-to-week variation in BNP and NT-proBNP is low in chronic heart failure patients during steady state, European Journal of Heart Failure, 2007, pp. 68-74, vol. 9.

Smith, M. W. et al., Delayed metabolism of human brain natriuretic peptide reflects resistance to neutral endopeptidase, Journal of Endocrinology, 2000, pp. 239-246, vol. 167.

Song, Hwa-Suk et al., Cardiac Troponin T Elevation After Stroke: Relationship Between Elevated Serum Troponin T, Stroke Location, and Prognosis, Journal of Clinical Neurology, 2008, pp. 75-83, vol. 4.

St. Croix, Brad et al., Genes Expressed in Human Tumor Endothelium, Science, 2000, pp. 1197-1202, vol. 289.

Tan, Mingjia et al., PTGF-β, a type β transforming growth factor (TGF-β) superfamily member, is a p53 target gene that inhibits tumor cell growth via TGF-β signaling pathway, Proceedings of the National Academy of Sciences, 2000, pp. 109-114, vol. 97, No. 1.

Tang, W. H. Wilson et al., National Academy of Clinical Biochemistry Laboratory Medicine Practice Guidelines: Clinical Utilization of Cardiac Biomarker Testing in Heart Failure, Circulation, 2007, pp. e99-e109, vol. 116.

Tang, W. H. Wilson et al., National Academy of Clinical Biochemistry Laboratory Medicine Practice Guidelines: Clinical Utilization of Cardiac Biomarker Testing in Heart Failure, Clinical Biochemistry, 2008, pp. 210-221, vol. 41.

Tasheva, Elena S. et al., Mimecan/osteoglycin-deficient mice have collagen fibril abnormalities, Molecular Vision, 2002, pp. 407-415, vol. 8.

Trooyen, M. et al., The use of cardiac troponin-1 to determine the incidence of myocardial injury in patients with acute stroke, Tidsskr Nor Laegefuren, 2001, pp. 421-425, vol. 121, No. 4, English abstract.

Tsuchida, Keizo and Tanabe, Kazuhiko, Influence of Paroxysmal Atrial Fibrillation Attack on Brain Natriuretic Peptide Secretion, Journal of Cardiology, 2004, pp. 1-11, vol. 44, No. 1.

Ustrell, Xavier and Pellisé, Anna, Cardiac Workup of Ischemic Stroke, Current Cardiology Reviews, 2010, pp. 175-183, vol. 6.

Van Den Bos, Ewout J. et al., Minor elevations in troponin I are associated with mortality and adverse cardiac events in patients with atrial fibrillation, European Heart Journal, 2011, pp. 611-617, vol. 32.

Van Der Worp, H. Bart and Van Gijn, Jan, Acute Ischemic Stroke, The New England Journal of Medicine, 2007, pp. 572-579, vol. 357.

Wachter, Rolf et al., Natriuretic Peptides for the Detection of Paroxysmal Atrial Fibrillation in Patients with Cerebral Ischemia—the Find-AF Study, PLoS One, 2012, e34351, 7 pps., vol. 7, Issue 4.

Wallace, Thomas W. et al., Prevalence and Determinants of Troponin T Elevation in the General Population, Circulation, 2006, pp. 1958-1965, vol. 113.

Williams, Eric M. et al., Use and Side-Effect Profile of Spironolactone in a Private Cardiologist's Practice, Clinical Cardiology, 2006, pp. 149-153, vol. 29.

Wu, Alan H. B. et al., Analytical and Clinical Evaluation of the Bayer ADVIA Centaur Automated B-Type Natriuretic Peptide Assay in Patients with Heart Failure: A Multisite Study, Clinical Chemistry, 2004, pp. 867-873, vol. 50, No. 5.

Xiong, Ya-qing et al., Effects of paroxysmal atrial fibrillation on plasma levels of brain natriuretic peptide in the elderly patients with essential hypertension, Practical Geriatrics, 2007, pp. 42-44, vol. 21 No. 1.

Yeh, Edward T. H., CRP as a Mediator of Disease, Circulation, 2004, pp. II-11-II-14, vol. 109 [suppl II].

Yeo, Kiang-Teck J. et al., Multicenter evaluation of the Roche NT-proBNP assay and comparison to the Biosite Triage BNP assay, Clinica Chimica Acta, 2003, pp. 107-115, vol. 338.

Yokoyama-Kobayashi, Midori et al., Human cDNA Encoding a Novel TGF-β Superfamily Protein Highly Expressed in Placenta, Journal of Biochemistry, 1997, pp. 622-626, vol. 122, No. 3.

Ülgen, A et al., The Relationship Between HSCRP Levels and P Wave Duration in Lone Paroxysmal Atrial Fibrillation Patients, International Journal of Cardiology, 2013, p. S22, vol. 163.

Di Angelantonio, E. et al., Prognostic significance of admission levels of troponin I in patients with acute ischaemic stroke, Journal of Neurology, Neurosurgery & Psychiatry, 2005, pp. 76-81, vol. 76.

Etgen, Thorleif et al., Cardiac Troponins and N-Terminal Pro-Brain Natriuretic Peptide in Acute Ichemic Stroke Do Not Relate to Clinical Prognosis, Stroke, 2005, pp. 270-275, vol. 36.

Fure, B. et al., Electrocardiographic and troponin T changes in acute ischaemic stroke, Journal of Internal Medicine, 2006, pp. 592-597, vol. 259.

Alter, Peter and Maisch, Bernhard, Non-compaction cardiomyopathy in an adult with hereditary sperocytosis, The European Journal of Heart Failure, 2007, pp. 98-99, vol. 9.

Cairns, John A. et al., Canadian Cardiovascular Society Atrial Fibrillation Guidelines 2010: Prevention of Stroke and Systemic Thromboembolism in Atrial Fibrillation and Flutter, Canadian Journal of Cardiology, 2011, pp. 74-90, vol. 27.

Camm, A. John et al., The Task Force for the Management of Atrial Fibrillation of the European Society of Cardiology (ESC), European Heart Journal, 2010, pp. 2369-2429, vol. 31.

Needleman, Saul B. and Wunsch, Christian D., A General Method Applicable to the Search for Similarities in the Amino Acid Sequence of Two Proteins, Journal of Molecular Biology, 1970, pp. 443-453, vol. 48.

Pearson, William R. and Lipman, David J., Improved tools for biological sequence comparison, Proceedings of the National Academy of Sciences USA, 1988, pp. 2444-2448, vol. 85.

Smith, Temple F. and Waterman, Michael S., Comparison of Biosequences, Advances in Applied Mathematics, 1981, pp. 482-489, vol. 2.

Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.

Marcus, Gregory M. et al., Markers of Inflammation Before and After Curative Ablation of Atrial Flutter, Heart Rhythm, 2008, pp. 215-221, vol. 5, No. 2.

Badran, Hala Mahfouz et al., Doppler-Derived Indexes and B-Type Natriuretic Peptide in Prediction of Paroxysmal Atrial Fibrillation in Essential Hypertension: A Prospective Study, Echocardiography, 2007, pp. 911-922, vol. 24, No. 9.

Ellinor, Patrick T. et al., Discordant Atrial Natriuretic Peptide and Brain Natriuretic Peptide Levels in Lone Atrial Fibrillation, Journal of the American College of Cardiology, 2005, pp. 82-86, vol. 45, No. 1.

Shin, D.-I. et al., Plasma levels of NT-pro-BNP in patients with atrial fibrillation before and after electrical cardioversion, Zeitschrift für Kardiologie, 2005, pp. 795-800, vol. 94.

Van Der Vekens, Nicky et al., Human and equine cardiovascular endocrinology: beware to compare,Cardiovascular Endocrinology, 2013, pp. 67-76, vol. 2, No. 4.

(56) References Cited

OTHER PUBLICATIONS

Benjamin et al., Prevention of Atrial Fibrillation; Report From a National Heart, Lung, and Blood Institute Workshop; 13-pages. Circulation, 119, 2009,.

De Lemos et al., Association of Troponin T Detected With a Highly Sensitive Assay and Cardiac Structure and Mortality Risk in the General Population; 10-pages. JAMA, 2010.

Scheitz et al., Troponin elevation in acute ischemic stroke (TRELAS)—protocol of a prospective observational trial; 7-pages.•BMC 11:98, 2011.

Saenger et al., Multicenter analytical evaluation of a high-sensitivity troponin T assay; 7-pages. Clinica Chimica Acta, 2011.

Thygesen et al., How to Use high-sensitivity cardiac troponins in acute cardiac care; 7-pages. European Heart. Journal, 2012.

Gahlmann et al., Differential Expression of Slow and Fast Skeletal Muscle Troponin C; J. Mol. Biol., 1998, 13-pages.

Hunt et al., ACC/AHA Practice Guidelines; 2001, 83-pages.

Oral Proceedings Feb. 23, 2021. Beschwerdekaramern Board of Chambers de reccurs pp. 1-7.

Ovoid: Clinical Laboratory Medicine; 22-pages. Myocardial and Skeletal Muscle disease, 2016.

Schotten et al., Pathophysiological Mechanisms of Atrial Febrillation: A Translational Appraisal; 61-pages. 2011.

Sundstrom et al., Cardiac troponin-I and risk of heart failure: a community-based cohort study; European Heart Journal, 2009, vol. 30, pp. 773-781.

Thygesen et al., Recommendations for the use of cardiac troponin measurement in acute cardiac care; European Heart Journal, 2010, 10-pages. European. Heart Journal, 2010.

Van Den Bos et al., Minor elevations in troponin I are associated with mortality and adverse cardiac events in patients with atrial fibrillation; European Heart Journal, 2011, 7-pages.

Zethelius et al., Troponin I as a Predictor of Coronary Heart Disease and Mortality in 70-Year-Old Men; Epidemiology; 8 pages. 2008 Opposition against EP Patent No. 2 002 260 (07 754 941.8). 3-pages. Aug. 2016.

Conrad et al., Cardiac Troponins and High-sensitivity Carciac Troponin Assays; 15-pages. Clin Lab Med 2014.

Shave et al., Exercise-Induced Cariac Troponin Elevation; 8-pages. Journal of the American College of Cardiology, vol. 56. No. 3, 2010.

Lowbeer et al., Serum cardiac troponin T, troponin I, plasma BNP and left ventricular mass index in professional football players; 6-pages. Journal of Science and Medicine in Sport, 2017.

Clinical Chemistry 57:1; Letters to the Editor; Cardiac Troponins T and I: Reproducible Discrepancies in the Clinical Setting; 3-pages. 2011.

Omland et al., Prognostic Value of Cardiac Troponin I Measured With a Highly Sensitive Assay in Patients with Stable Coronary Artery Disease; 10-pages. Journal of the American College of Cardiology 2013. .

Klinkenberg et al., Diurnal Rhythm of Cardiac Troponin: Consequences for the Diagnosis of Acute Myocardial Infarction; 10-pages. Clinical Chemistry 2016.

Rienstra et al., Symptoms and Functional Status of Patients With Atrial Fibrillation; 11-pages. Circulation, 2012.

Communication of a notice of Opposition; 16175468.4-1111/3088900; dated May 18, 2021.

Mallamaci et al., Troponin is Related to Left Ventricular Mass and Predicats All-Cause and Cardiovascular Mortality in Hemodialysis Patients; 8-pages. 2002.

* cited by examiner

TROPONIN AND BNP BASED DIAGNOSIS OF RISK PATIENTS AND CAUSE OF STROKE

CROSS-REFERENCE TO RELATED APPLICATIONS

This application is a continuation of U.S. application Ser. No. 15/285,798 filed Oct. 5, 2016 (now abandoned), which is a continuation of U.S. application Ser. No. 14/859,616 filed Sep. 21, 2015 (abandoned), which is a continuation of U.S. application Ser. No. 14/251,803 filed Apr. 14, 2014 (abandoned), which is a continuation of International Application No. PCT/EP2012/070553, filed Oct. 17, 2012, which claims the benefit of European Patent Application No. 11185421.2, filed Oct. 17, 2011, the disclosures of which are hereby incorporated by reference in their entirety.

BACKGROUND OF THE DISCLOSURE

Stroke ranks after ischemic heart disease second as a cause of lost disability—adjusted life—years in high income countries and as a cause of death worldwide. If presented early adverse consequences of stroke can be ameliorated using thrombolysis, in case of late presentation secondary prevention (to prevent subsequent stroke) using aspirin and anticoagulation appears the only appropriate method to avoid disease progression (van der Worp B and van Gijn J., NEJM 2007: 357: 572-578).

In order to prevent or treat stroke the identification of the underlying cause of stroke is of importance. This has been addressed by the TOAST criteria (Adams H. P. et al Stroke 1993: 24: 35-41). TOAST criteria dissect causes of stroke into atherothrombotic (atherosclerosis of large vessels), cardioembolic, lacunar (involving small vessels) and undetermined (Adams H. P. et al). In order to assess these criteria carotid and transcranial ultrasound are required as well as echocardiography and an electrocardiogram (Rodriguez-Yanez et al, Disease Markers 2009: 26: 189-195).

Cardiac troponins T and I are the preferred biomarkers for the diagnosis of acute myocardial infarction (Anderson J L, ACC/AHA 2007 guidelines for the management of patients with unstable angina/non-ST-Elevation myocardial infarction. J Am Coll Cardiol. 2007; 50(7):e1-e157). It has been recognized that elevated troponin levels may be detected in several non-acute chronic disease states, including coronary artery disease, heart failure, and chronic kidney disease (see e.g. Omland et al., N Engl J Med. 2009; 361(26):2538-2547). Troponins T and I are also been shown to be detectable in individuals from the general population (see e.g. Wallace et al., Prevalence and determinants of troponin T elevation in the general population. Circulation. 2006; 113(16):1958-1965).

SUMMARY OF THE DISCLOSURE

The present disclosure relates to a method for early differentiating whether a subject suffers from cardioembolic stroke or from non-cardioembolic ischemic stroke. The method is based on the determination of the amount of a cardiac Troponin in a sample from a subject suffering from ischemic stroke obtained not more than 24 hours after the onset of symptoms of ischemic stroke. Moreover, the present disclosure relates to a method for diagnosing atrial fibrillation in a subject. Further envisaged by the present disclosure are kits and devices adapted to carry out the method of the present disclosure. The present disclosure also relates to a system for early differentiating whether a subject suffers from cardioembolic stroke or from non-cardioembolic ischemic stroke and for diagnosing atrial fibrillation. Further, the present disclosure relates to reagents and kits used in performing the methods disclosed herein.

In the context of the present disclosure, it has been surprisingly shown that elevated cardiac Troponin levels in patients with cardioembolic stroke are detectable already at the onset of cardioembolic stroke. Thus, the increase of the level of cardiac Troponins is not caused by the stroke event. Rather, the studies of the present disclosure suggest that the levels of cardiac troponins are already increased before the onset of stroke symptoms. Therefore, the determination of cardiac Troponins allows for an early differentiation between cardioembolic ischemic stroke and non-cardioembolic ischemic stroke in the subject. This is advantageous since the early assessment of the cause of stroke is crucial in order to sufficiently treat a subject suffering from stroke, in particular a subject suffering from cardioembolic stroke. Moreover, strokes due to cardioembolism are in general severe and prone to early recurrence

DETAILED DESCRIPTION OF THE EMBODIMENTS OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Conventional diagnostic techniques usually do not allow for an early, reliable assessment of the cause of stroke. Accordingly, a personalized treatment regimen cannot be determined with sufficient accuracy. As a consequence thereof, many patients will receive a treatment regimen which is insufficient or which may have adverse side effects. Therefore, means and methods are required for reliably differentiating between the causes of stroke.

Accordingly, the present disclosure method for early differentiating whether a subject suffers from cardioembolic stroke or from non-cardioembolic ischemic stroke, comprising a) determining the amount of a cardiac Troponin in a sample from a subject suffering from ischemic stroke, wherein the sample has been obtained immediately after the onset of symptoms of ischemic stroke.

In an exemplary embodiment the method further comprising the step of b) comparing the amount of said cardiac Troponin as determined in step a to a reference amount, thereby differentiating whether said subject suffers from cardioembolic stroke or from non-cardioembolic ischemic stroke.

Thus, the present disclosure, in particular, relates to a method for early differentiating whether a subject suffers from cardioembolic stroke or from non-cardioembolic ischemic stroke, comprising a) determining the amount of a cardiac Troponin in a sample from a subject suffering from ischemic stroke, obtained immediately after the onset of symptoms of ischemic stroke, and b) comparing the amount of said cardiac Troponin as determined in step a) to a reference amount, whereby it is differentiated whether said subject suffers from cardioembolic ischemic stroke or from non-cardioembolic ischemic stroke.

According to exemplary embodiments, it is differentiated, whether a subject suffers from cardioembolic ischemic stroke or from non-cardioembolic ischemic stroke by carrying out the further step of c) diagnosing whether a subject suffers from cardioembolic ischemic stroke or from non-cardioembolic ischemic stroke, based on the results of the comparison carried out in step b).

In an exemplary embodiment of the method of the present disclosure, step a) further comprises the determination of the amount of a natriuretic peptide in the sample from the subject obtained immediately after the onset of ischemic stroke. Thus, according to exemplary embodiments, the determined amount of the natriuretic peptide is compared in step b) to a reference amount for a natriuretic peptide.

Thus, the present disclosure also relates to a method for early differentiating whether a subject suffers from cardioembolic stroke or from non-cardioembolic ischemic stroke, comprising
 a) determining the amount of a cardiac Troponin and of natriuretic peptide in a sample from a subject suffering from ischemic stroke, obtained immediately after the onset of symptoms of ischemic stroke, and
 b) comparing the amount of said cardiac Troponin as determined in step a) to a reference amount for the cardiac Troponin, and the amount of said natriuretic peptide to a reference amount for the natriuretic peptide, whereby it is differentiated whether said subject suffers from cardioembolic stroke or from non-cardioembolic ischemic stroke.

The method of the present disclosure, may include, is an ex vivo method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the determination in step (a) or a computer-implemented comparison and/or differentiation based on said comparison in step (b).

Accordingly, the present disclosure also preferably relates to a system for early differentiating whether a subject suffers from cardioembolic ischemic stroke or from non-cardioembolic ischemic stroke, comprising
 a) an analyzer unit configured to contact, in vitro, a portion of a sample from a subject who suffers from ischemic stroke with a ligand comprising specific binding affinity for a cardiac Troponin,
 b) an analyzer unit configured to detect a signal from the portion of the sample from the subject contacted with the ligand,
 c) a computing device having a processor and in operable communication with said analysis units, and
 d) a non-transient machine readable media including a plurality of instruction executable by a processor, the instructions, when executed calculate an amount of the cardiac Troponin, and compare the amount of the marker with a reference amount, thereby differentiating whether a subject suffers from cardioembolic ischemic stroke or from non-cardioembolic ischemic stroke.

The term "differentiating" as used herein means to distinguish between cardioembolic stroke and non-cardioembolic stroke in a patient suffering from ischemic stroke. The term as used herein, preferably, includes differentially diagnosing cardioembolic ischemic stroke and non-cardioembolic ischemic stroke in a subject. As will be understood by those skilled in the art, such an assessment is usually not intended to be correct for 100% of the subjects to be differentially diagnosed. The term, however, requires that a statistically significant portion of subjects can be correctly diagnosed. Whether a diagnosis/differentiation is correct can be confirmed by methods well known in the art. Moreover, whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

The term "subject" as used herein relates to animals, preferably mammals, and, more preferably, humans. Preferably, the subject does or not suffer from acute infections. Moreover, it is further envisaged that the subject does not suffer from acute coronary syndrome and/or from chronic renal failure. In particular, the subject in the context with the aforementioned method shall have normal kidney function. Furthermore, the subject is, preferably, a subject presenting to an emergency unit.

The definition of the subject given herein, preferably, applies to the subject to be tested in accordance with the method of the present disclosure as well as to the subject/subjects from which the reference amount is derived.

The subject to be tested in accordance with the method of the present disclosure shall suffer from ischemic stroke. The term "ischemic stroke" (herein also referred to as "stroke") is well known by the skilled person (see e.g. Adams et al., Guidelines for the Early Management of Adults With Ischemic Stroke, A Guideline From the American Heart Association/American Stroke Association Stroke Council, Clinical Cardiology Council, Cardiovascular Radiology and Intervention Council, and the Atherosclerotic Peripheral Vascular Disease and Quality of Care Outcomes in Research Interdisciplinary Working Groups in Stroke. 2007; 38:1655; or Stroke Genetics, edited by Hugh S. Markus, Chapter 1 "An introduction to stroke, Oxford University Press, Incorporated, Publish Date June 2003, both of which are herewith incorporated by reference with respect to its entire disclosure content). As used herein, the term, preferably, refers to cerebral ischemic stroke. Ischemic stroke is caused by reduced blood flow to the brain or parts thereof which leads to a reduced delivery (undersupply) of oxygen to brain cells. Ischemic stroke may be characterized by tissue anemia caused by obstruction of the inflow of arterial blood. It may lead to irreversible tissue damage due to brain cell death.

There are various classification systems for ischemic stroke. The Oxford Community Stroke Project classification (OCSP, also known as the Bamford or Oxford classification) relies primarily on the initial symptoms; based on the extent of the symptoms, the stroke episode is classified as total anterior circulation infarct (TACI), partial anterior circulation infarct (PACI), lacunar infarct (LACI) or posterior circulation infarct (POCI). These four entities predict the extent of the stroke, the area of the brain affected, the underlying cause, and the prognosis.

Preferably, the so called TOAST criteria are applied herein. For the TOAST criteria, see e.g. Donnan G A, Fisher M, Macleod M, Davis S M (May 2008). "Stroke". Lancet 371 (9624): 1612-23 or "Classification of subtype of acute ischemic stroke. Definitions for use in a multicenter clinical trial. TOAST. Trial of Org 10172 in Acute Stroke Treatment". Stroke 24 (1): 35-41, both of which are herein incorporated by reference with respect to the entire disclosure content. The TOAST (Trial of Org 10172 in Acute Stroke Treatment) classification is based on clinical symptoms as well as results of further investigations; on this basis, a stroke is classified as being due to (1) embolism of cardiac origin (cardioembolic stroke) (2) thrombosis or embolism due to atherosclerosis of a large artery (large artery stenosis, atherothrombotic stroke), (3) occlusion of a small blood vessel (lacunar stroke) or (4) undetermined cause (two possible causes: no cause identified, or incomplete investigation). Thus, preferred non-cardioembolic ischemic strokes are atherothrombotic stroke (see 2) and lacunar stroke (see 3).

Whether a subject suffers from stroke, in particular from ischemic stroke can be determined by well-known methods. Moreover, symptoms of stroke are well known in the art and e.g. described in Adams et al. (loc. cit.). E.g., stroke symptoms include sudden numbness or weakness of face, arm or leg, especially on one side of the body, sudden confusion, trouble speaking or understanding, sudden trouble seeing in one or both eyes, and sudden trouble walking, dizziness, loss of balance or coordination.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

The sample to be tested in the context of the method of the present disclosure shall have been obtained immediately after the onset of symptoms of stroke (as well as the reference sample). Preferably, a sample is deemed to have been obtained immediately after the onset of symptoms of stroke if it has been obtained from said subject not more than 24 hours, in particular not more than 12 hours after the onset of symptoms of stroke. More preferably, a sample is deemed to have been obtained immediately after the onset of symptoms of stroke if it has been obtained from said subject not more than 6 hours, and even more preferably not more than 3 hours after the onset of symptoms of ischemic stroke. Further envisaged is that the sample has been obtained not more than one or two hours after the onset of stroke symptoms.

The term "cardiac Troponin" refers to all Troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac Troponin refers to Troponin T and/or Troponin I, and, most preferably, to Troponin T. It is to be understood that isoforms of Troponins may be determined in the method of the present disclosure together, i.e. simultaneously or sequentially, or individually, i.e. without determining the other isoform at all. Amino acid sequences for human Troponin T and human Troponin I are disclosed in Anderson, loc cit and Ferrieres 1998, Clinical Chemistry, 44: 487-493.

The term "cardiac Troponin" encompasses also variants of the aforementioned specific Troponins, i.e., preferably, of Troponin I, and more preferably, of Troponin T. Such variants have at least the same essential biological and immunological properties as the specific cardiac Troponins. In particular, they share the same essential biological and immunological properties if they are detectable by the same specific assays referred to in this specification, e.g., by ELISA Assays using polyclonal or monoclonal antibodies specifically recognizing the said cardiac Troponins. Moreover, it is to be understood that a variant as referred to in accordance with the present disclosure shall have an amino acid sequence which differs due to at least one amino acid substitution, deletion and/or addition wherein the amino acid sequence of the variant is still, preferably, at least about 50%, at least about 60%, at least about 70%, at least about 80%, at least about 85%, at least about 90%, at least about 92%, at least about 95%, at least about 97%, at least about 98%, or at least about 99% identical with the amino sequence of the specific Troponin. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants may be allelic variants or any other species specific homologs, paralogs, or orthologs. Moreover, the variants referred to herein include fragments of the specific cardiac Troponins or the aforementioned types of variants as long as these fragments have the essential immunological and biological properties as referred to above. Preferably, the cardiac troponin variants have immunological properties (i.e. epitope composition) comparable to those of human troponin T or troponin I. Thus, the variants shall be recognizable by the aforementioned means or ligands used for determination of the concentration of the cardiac troponins. Thus, the variants shall be recognizable by the aforementioned means or ligands used for determination of the concentration of the cardiac troponins. Such fragments may be, e.g., degradation products of the Troponins. Further included are variants which differ due to posttranslational modifications such as phosphorylation or myristylation. Preferably the biological property of troponin I and its variant is the ability to inhibit actomyosin ATPase or to inhibit angiogenesis in vivo and in vitro, which may e.g. be detected based on the assay described by Moses et al. 1999 PNAS USA 96 (6): 2645-2650). Preferably the biological property of troponin T and its variant is the ability to form a complex with troponin C and I, to bind calcium ions or to bind to tropomyosin, preferably if present as a complex of troponin C, I and T or a complex formed by troponin C, troponin I and a variant of troponin T. It is known that low concentrations of circulating cardiac troponin may be detected in subjects at various conditions, but further studies are required to understand their respective role and rate (Masson et al., Curr Heart Fail Rep (2010) 7:15-21).

The term "natriuretic peptide" comprises Atrial Natriuretic Peptide (ANP)-type and Brain Natriuretic Peptide (BNP)-type peptides and variants thereof having the same predictive potential. Natriuretic peptides according to the present disclosure comprise ANP-type and BNP-type peptides and variants thereof (see e.g. Bonow, 1996, Circulation 93: 1946-1950). ANP-type peptides comprise pre-proANP, proANP, NT-proANP, and ANP. BNP-type peptides comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP). Preferably, natriuretic peptides according to the present disclosure are NT-proANP, ANP, and, more preferably, NT-proBNP, BNP, and variants thereof. ANP and BNP are the active hormones and have a shorter half-life than their respective inactive counterparts, NT-proANP and NT-proBNP. BNP is metabolized in the blood, whereas NT-proBNP circulates in the blood as an intact molecule and as such is eliminated renally. The in-vivo half-life of NT-proBNP is 120 min longer than that of BNP, which is 20 min (Smith 2000, J Endocrinol. 167: 239-46). Preanalytics are more robust with NT-proBNP allowing easy transportation of the sample to a central laboratory (Mueller 2004, Clin Chem Lab Med 42: 942-4). Blood samples can be stored at room temperature for several days or may be mailed or shipped without recovery loss. In contrast, storage of BNP for 48 hours at room temperature or at 4° Celsius leads to a concentration loss of at least 20% (Mueller loc.cit.; Wu 2004, Clin Chem 50: 867-73). Therefore, depending on the time-course or properties of interest, either measurement of the active or the inactive forms of the natriuretic peptide can be advantageous. The most preferred natriuretic peptides according to the present disclosure are NT-proBNP or variants thereof. As briefly discussed above, the human NT-proBNP, as referred to in accordance with the present disclosure, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present disclosure further encompasses allelic and other variants of said specific sequence for human NT-proBNP discussed above. Specifically, envisaged are variant polypeptides which are on the amino acid level preferably, at least 50%, 60%, 70%, 80%, 85%, 90%, 92%, 95%, 97%, 98%, or 99% identical to human NT-proBNP, preferably over the entire length of human NT-proBNP. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. Preferably, the NT-proBNP variants have immunological properties (i.e. epitope composition) comparable to those of human NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Lab Invest 230:177-181), Yeo et al. (Yeo 2003, Clinica Chimica Acta 338:107-115). Variants also include posttranslationally modified peptides such as glycosylated peptides. Further, a variant in accordance with the present disclosure is also a peptide or polypeptide which has been modified after collection of the sample, for example by covalent or non-covalent attachment of a label, particularly a radioactive or fluorescent label, to the peptide.

Determining the amount of a peptide or polypeptide referred to in this specification relates to measuring the amount or concentration, preferably, semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present disclosure, determining the amount of a peptide or polypeptide can be achieved by all known means for determining the amount of a peptide in a sample. Said means comprise immunoassay and methods which may utilize labeled molecules in various sandwich, competition, or other assay formats. Such assays are, preferably, based on detection agents such as antibodies which specifically recognize the peptide or polypeptide to be determined. The detection agents shall be either directly or indirectly capable of generating a signal indicating the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Preferably, determining the amount of a peptide or polypeptide comprises the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand.

According to a preferred embodiment, said steps of contacting, removing and measuring may be performed by an analyzer unit of the system disclosed herein. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The bound ligand, in particular the ligand or the ligand/peptide complex, will generate an intensity signal. Binding according to the present disclosure includes both covalent and non-covalent binding. A ligand according to the present disclosure can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)2 fragments that are capable of binding antigen or hapten. The present disclosure also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present disclosure means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Further suitable techniques for the determination of a polypeptide or peptide are described in the following.

First, binding of a ligand may be measured directly, e.g. by NMR or surface plasmon resonance. Measurement of the binding of a ligand, according to preferred embodiments, is performed by an analyzer unit of a system disclosed herein. Thereafter, an amount of the measured binding may be calculated by a computing device of a system disclosed herein. Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable lable prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured. Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g. a light-sensitive film or a phosphor imager. Suitable measurement methods according the present disclosure also include precipitation (particularly immunoprecipitation), electrochemiluminescence (electrogenerated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the disclosure. Suitable methods for fixing/immobilizing said ligand are well known and include, but are not limited to ionic, hydrophobic, covalent interactions and the like. It is also contemplated to use "suspension arrays" as arrays according to the present disclosure (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts determined from biological read out systems in response to the peptides or intensity signals obtained from specifically bound ligands. It is to be understood that values correlating to the aforementioned amounts or parameters can also be obtained by all standard mathematical operations. According to preferred embodiments of the subject disclosure, the determination of an "amount" is performed by the disclosed system, whereby a computing device determines the "amount" based on contacting and measuring steps performed by one or more analyzer units of said system.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present disclosure may be carried out manually or computer assisted. Thus, the comparison referred to in step (b) of the method of the present disclosure may be carried out by a computing device (e.g., of a system disclosed herein). The value of the amount and the reference can be, e.g., compared to each other and the said comparison can be automatically carried out by a computer program executing an algorithm for the comparison. The computer program carrying out the said evaluation will provide the desired assessment in a suitable output format. For a computer assisted comparison, the value of the determined amount may be compared to values corresponding to suitable references which are stored in a database by a computer program. The computer program may further evaluate the result of the comparison, i.e. automatically provide the desired assessment in a suitable output format.

For a computer assisted comparison, the value of the determined amount may be compared to values corresponding to suitable references which are stored in a database by a computer program. The computer program may further evaluate the result of the comparison, i.e. automatically provides the desired assessment in a suitable output format. The said result may, preferably, serve as an aid in differentiating between cardioembolic and non-cardioembolic ischemic stroke.

For example, a result of a comparison may be given as raw data (absolute or relative amounts), and in some cases as an indicator in the form of a word, phrase, symbol, or numerical value which may be indicative of a particular diagnosis.

The term "reference amount" as used herein refers to an amount which allows for allocation of a subject into either the group of subjects suffering from cardioembolic ischemic stroke or into a group of subject suffering from non-cardioembolic ischemic stroke. Such a reference amount can be a threshold amount which separates these groups from each other. Accordingly, the reference amount for a the biomarker Troponin shall be an amount which allows for allocation of a subject into a group of subjects suffering from cardioembolic ischemic stroke or into a group of subjects suffering from non-cardioembolic ischemic stroke. A suitable threshold amount separating the two groups can be calculated without further ado by the statistical tests referred to herein elsewhere based on amounts of a cardiac Troponin from either a subject or group of subjects suffering from cardioembolic ischemic stroke or a subject or group of subjects suffering from non-cardioembolic ischemic stroke. Preferred referenced amounts which can be derived from the aforementioned subjects or group of subjects are indicated elsewhere herein.

Reference amounts can, in principle, be calculated for a cohort of subjects as specified above based on the average or mean values for a given biomarker by applying standard statistically methods. In particular, accuracy of a test such as a method aiming to diagnose an event, or not, is best described by its receiver-operating characteristics (ROC) (see especially Zweig 1993, Clin. Chem. 39:561-577). The ROC graph is a plot of all of the sensitivity/specificity pairs resulting from continuously varying the decision threshold over the entire range of data observed. The clinical performance of a diagnostic method depends on its accuracy, i.e. its ability to correctly allocate subjects to a certain prognosis or diagnosis. The ROC plot indicates the overlap between the two distributions by plotting the sensitivity versus 1-specificity for the complete range of thresholds suitable for making a distinction. On the y-axis is sensitivity, or the true-positive fraction, which is defined as the ratio of number of true-positive test results to the product of number of true-positive and number of false-negative test results. This has also been referred to as positivity in the presence of a disease or condition. It is calculated solely from the affected subgroup. On the x-axis is the false-positive fraction, or 1-specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis or prediction for a given event with a proper balance of sensitivity and specificity, respectively. Accordingly, the reference to be used for the aforementioned method of the present disclosure can be, preferably, a threshold or cut off amount and can be generated, preferably, by establishing a ROC for said cohort as described above and deriving a threshold amount therefrom. Dependent on a desired sensitivity and specificity for a diagnostic method, the ROC plot allows deriving suitable thresholds.

The diagnosis/differentiation referred to herein may be provided by the computing device of a system disclosed herein based on said comparison of the calculated "amount" to a reference or a threshold. For example, a computing device of a system may provide an indicator, in the form of a word, symbol, or numerical value which is indicative of one cardioembolic stroke or non-cardioembolic stroke.

Preferably, the reference amount(s) is (are) derived from a subject or a group of subjects known to suffer from cardioembolic ischemic stroke. In this case, an essentially identical amount or an increased amount of a cardiac Troponin in the test sample as compared to reference amount is, preferably, indicative for cardioembolic ischemic stroke. If also a natriuretic peptide is determined, an essentially identical amount or an increased amount of a cardiac Troponin and of the natriuretic peptide in the test sample as compared to reference amount for the cardiac Troponin and the reference amount for the natriuretic peptide is, preferably, indicative for cardioembolic ischemic stroke.

Also preferably, the reference amount for a cardiac Troponin (and, optionally, of the natriuretic peptide) may be derived from a subject or a group of subjects known to suffer from non-cardioembolic ischemic stroke. In this case, an essentially identical amount or a decreased amount of the cardiac Troponin (and, optionally, of the natriuretic peptide) in the test sample as compared to reference amount is indicative for non-cardioembolic ischemic stroke. If also a natriuretic peptide is determined, an essentially identical amount or a decreased amount of the cardiac Troponin of the natriuretic peptide in the test sample as compared to the reference amount for the cardiac Troponin and the reference amount for the natriuretic peptide is indicative for non-cardioembolic ischemic stroke.

The reference amount applicable for an individual subject may vary depending on various physiological parameters such as age, gender, or subpopulation, as well as on the means used for the determination of the polypeptide or peptide referred to herein. A suitable reference amount may be determined from a reference sample to be analyzed together, i.e. simultaneously or subsequently, with the test sample.

Further, the reference amount may define a threshold amount, in particular a calculated reference amount, for the cardiac Troponin (and, optionally for the natriuretic peptide), whereby an amount of Troponin (and, optionally of the natriuretic peptide) in the sample of the test subject larger than the respective threshold shall be indicative for cardioembolic ischemic stroke, while an amount of Troponin (and, optionally, of the natriuretic peptide) in the sample of the test subject lower than the respective threshold shall be indicative for non-cardioembolic stroke.

Preferred reference amounts are indicated herein below.

A preferred reference amount indicating cardioembolic ischemic stroke is an amount of a cardiac troponin, in particular of Troponin T of about 8 pg/ml to about 40 pg/ml and, more preferably, 10 to 30 pg/ml, about 11.6 to about 20 pg/ml, even more preferably of about 15 to 20 pg/ml. Even more preferably, the reference is an amount of about 8, 10, or 11.6 pg/ml. A test amount being essentially identical or increased shall be indicative for cardioembolic ischemic stroke while a decreased amount in the test sample as compared to the reference amount shall be indicative for non-cardioembolic ischemic stroke. Preferably, the aforementioned reference amounts are derived from a subject or a group of subjects known to suffer from cardioembolic ischemic stroke.

The present disclosure is, particularly, useful for ruling out cardioembolic stroke. In particular, a test amount of a cardiac Troponin, preferably, of Troponin T, being lower than 5 pg/ml, in particular lower than 3 or lower than 2 pg/mg indicates that the subject does not suffer from cardioembolic stroke (and, thus, preferably, suffers from non-cardioembolic stroke).

A preferred reference amount indicating cardioembolic ischemic stroke is an amount of a natriuretic peptide, in particular, of NT-proBNP of about 500 pg/ml to about 1500 pg/ml and, more preferably, 700 to 1300 pg/ml, even more preferably of about 800 to 1000 pg/ml. Even more preferably, the reference is an amount of about 700, 800, or most preferably 900 pg/ml. A test amount being essentially identical or increased shall be indicative for cardioembolic ischemic stroke while a decreased amount in the test sample as compared to the reference amount shall be indicative for non-cardioembolic ischemic stroke. Preferably, the aforementioned reference amounts are derived from a subject or a group of subjects known to suffer from cardioembolic ischemic stroke (in addition to the amount of the cardiac Troponin).

As set forth above, the present disclosure is, particularly, useful for ruling out cardioembolic stroke. In particular, a test amount of a natriuretic peptide, in particular of NT-proBNP being lower than 250 pg/ml, in particular lower than 200 or lower than 150 pg/mg indicates that the subject does not suffer from cardioembolic stroke (and, thus, preferably, suffers from non-cardioembolic stroke).

The term "about" in the context of the present disclosure means +/−20%, +/−10%, +/−5%, +/−2% or +/−1% from the said values. This also takes into account usual deviations caused by measurement techniques, statistics and the like.

In some embodiments of the method of the present disclosure, said method further comprises recommending a therapy for said subject, in particular, if the subject has been diagnosed to suffer from cardioembolic stroke. A therapy that can be recommended in a subject who suffers from cardioembolic stroke is lytic therapy and/or anticoagulation therapy (see e.g. Cairns J. A. et al Canadian J of Cardiology 2011: 27: 74-90 or Camm A. J. et al Eur Heart Journal 2010: 31: 2369-429 which are both incorporated herein by reference).

In an aspect of the disclosure, a method for differentiating whether a subject suffers from cardioembolic ischemic stroke or from non-cardioembolic ischemic stroke, is contemplated, said method comprising:
  a) determining the amount of a cardiac Troponin in a sample from a subject suffering from ischemic stroke by (i) bringing the sample into contact with a detection agent that specifically binds to said cardiac Troponin for a time sufficient to allow for the formation of a complex of the said detection agent and the cardiac Troponin from the sample, (ii) measuring the amount of the formed complex, wherein the said amount of the formed complex is proportional to the amount of the at cardiac Troponin present in the sample, and (iii) transforming the amount of the formed complex into an amount of the cardiac Troponin reflecting the amount of the marker present in the sample;
  b) comparing said amount to a reference; and
  c) establishing an aid for differentiating whether a subject suffers from cardioembolic ischemic stroke or from non-cardioembolic ischemic stroke, based on the result of the comparison made in step b).

Preferably, also the amount of a natriuretic peptide is determined.

In another aspect of the disclosure, a system for differentiating whether a subject suffers from cardioembolic ischemic stroke or from non-cardioembolic ischemic stroke, is contemplated, comprising:
  a) an analyzer unit configured to bringing a sample from a subject who suffers from ischemic stroke into contact with a detection agent that specifically binds to the marker cardiac Troponin for a time sufficient to allow for the formation of a complex of the said detection agent and the marker from the sample,
  b) an analyzer unit configured to measure the amount of the formed complex, wherein the said amount of the formed complex is proportional to the amount of the marker present in the sample,
  c) a computing device having a processor and in operable communication with said analysis units, and
  d) a non-transient machine readable media including a plurality of instructions executable by the processor, the instructions, when executed transform the amount of the formed complex into an amount of the marker reflecting the amount of the marker present in the sample, compare said amount to a reference, and establish an aid for differentiating whether a subject suffers from cardioembolic ischemic stroke or from non-cardioembolic ischemic stroke based on the result of said comparison to said reference.

Preferably, the system also comprises a detection agent that specifically binds to natriuretic peptide.

A suitable detection agent may be, in an aspect, an antibody which is specifically binds to the cardiac troponin, in a sample of a subject to be investigated by the method of the disclosure. Another detection agent that can be applied, in an aspect, may be an aptamere which specifically binds to the marker in the sample. In yet an aspect the, sample is removed from the complex formed between the detection agent and the marker prior to the measurement of the amount of formed complex. Accordingly, in an aspect, the detection agent may be immobilized on a solid support. In yet an aspect, the sample can be removed from the formed complex on the solid support by applying a washing solution. The formed complex shall be proportional to the amount of the marker present in the sample. It will be understood that the specificity and/or sensitivity of the detection agent to be applied defines the degree of proportion of at least one marker comprised in the sample which is capable of being specifically bound. Further details on how the determination can be carried out are also found elsewhere herein. The amount of formed complex shall be transformed into an amount of the marker reflecting the amount indeed present in the sample. Such an amount, in an aspect, may be essentially the amount present in the sample or may be, in another aspect, an amount which is a certain proportion thereof due to the relationship between the formed complex and the amount present in the original sample.

In yet an aspect of the aforementioned method, step a) may be carried out by an analyzer unit, in an aspect, an analyzer unit as defined elsewhere herein.

In an aspect of the method of the disclosure, the amount determined in step a) is compared to a reference. In an aspect, the reference is a reference as defined elsewhere herein. In yet another aspect, the reference takes into account the proportional relationship between the measured amount of complex and the amount present in the original sample. Thus, the references applied in an aspect of the method of the disclosure are artificial references which are adopted to reflect the limitations of the detection agent that has been used. In another aspect, said relationship can be also taken into account when carrying out the comparison, e.g., by including a normalization and/or correction calculation step for the determined amount prior to actually comparing the value of the determined amount and the reference. Again, the normalization and/or correction calculation step for the determined amount adopts the comparison step such that the limitations of the detection agent that has been used are reflected properly. In an aspect, the comparison is carried out automatically, e.g., assisted by a computer system or the like.

The aid for differentiating whether a subject suffers from cardioembolic ischemic stroke or from non-cardioembolic ischemic stroke is established based on the comparison carried out in step b) by allocating the subject either (i) the group of subjects who suffer from cardioembolic stroke or (ii) the group of who suffer from non-cardioembolic stroke as set forth herein elsewhere. As discussed elsewhere herein already, the allocation of the investigated subject must not be correct in 100% of the investigated cases. Moreover, the groups of subjects into which the investigated subject is allocated are artificial groups in that they are established based on statistical considerations, i.e. a certain preselected degree of likelihood based on which the method of the disclosure shall operate. In an aspect of the disclosure, the aid for the differentiation is established automatically, e.g., assisted by a computing device or the like, as described and disclosed herein.

In an aspect of the method of the disclosure, said method further comprises a step of recommending and/or managing the subject according to the result established in step c) as set forth elsewhere herein in detail.

In an aspect of the aforementioned method, steps b) and/or c) are carried out by one or more analyzer units as set forth elsewhere herein.

Method for Diagnosing Atrial Fibrillation

Atrial fibrillation (AF) is frequently no recognised by the patient. This is the case in approximately 40% of patients indicating that history taking in insensitive for the diagnosis of atrial fibrillation (Kamel H. et al, Curr Atheroscler Rep 2011: 13: 338-343). While these numbers relate to persistent atrial fibrillation, paroxysmal atrial fibrillation is even more difficult to diagnose and can only be captured by inpatient cardiac telemetry or even Jolter Monitoring. The latter having the advantage, that the ECG is recorded and can later on be reviewed by an experienced physician. Using Holter ECG paroxysmal—previously unrecognised atrial fibrillation was more frequent than persistent atrial fribillation (Rizos T. et all. Cerebrovasc. Dis 2011: 32: 276-282). In order to capture paroxysmal/ischemic atrial fibrillation reliably 72 h Holter monitoring appears necessary (Gumbinger C et al, Europ. J of Neurology 2011 ahead of publication). Thus recognition of paroxysmal atrial fibrillation is a significant challenge, specifically as at least 1% of the general population has persistent atrial fibrillation and the frequency increases with age (Rizos T. et al).

The inventors have found that the determination of a cardiac Troponin allows for diagnosing atrial fibrillation. Interestingly, patients with intermittent AF had also increased cardiac Troponin levels. Therefore, also patients exhibiting intermittent AF can be identified by determining the amount of cardiac Troponin.

The definitions and explanations given herein above apply mutatis mutandis to the following embodiments of the present disclosure.

Moreover, the present disclosure relates to a method for diagnosing atrial fibrillation in a subject suspected to suffer from atrial fibrillation, comprising a) determining the amount of a cardiac Troponin in a sample from said subject.

In a preferred embodiment the method comprises the further step of
  b) comparing the, thus, determined amount of said cardiac Troponin to a reference amount. Thereby, intermittent atrial fibrillation is diagnosed.

Accordingly, the present disclosure relates to a method for diagnosing atrial fibrillation in a subject suspected to suffer from atrial fibrillation, comprising
  a) determining the amount of a cardiac Troponin in a sample from said subject, and
  b) comparing the, thus, determined amount of said cardiac Troponin to a reference amount, whereby atrial fibrillation is diagnosed.

Preferably, it is diagnosed whether a subject suffers from atrial fibrillation, or not, by carrying out the further step c) of diagnosing whether the subject suffers from atrial fibrillation, or not.

Preferably, intermittent atrial fibrillation is diagnosed.

Accordingly, the present disclosure, in particular relates to a method for diagnosing intermittent atrial fibrillation in a subject suspected to suffer from atrial fibrillation, comprising
   a) determining the amount of a cardiac Troponin in a sample from said subject, and
   b) comparing the, thus, determined amount of said cardiac Troponin to a reference amount, whereby intermittent atrial fibrillation is diagnosed.

In a preferred embodiment of the method of the present disclosure, step a) further comprises the determination of the amount of a natriuretic peptide in the sample from the subject. Preferably, the, thus, determined amount of the natriuretic peptide is compared in step b) to a reference amount for a natriuretic peptide.

Thus, the present disclosure also relates to a method for diagnosing atrial fibrillation in a subject suspected to suffer from atrial fibrillation, comprising
   a) determining the amount of a cardiac Troponin and of natriuretic peptide in a sample from said subject, and
   b) comparing the amount of said cardiac Troponin as determined in step a) to a reference amount for the cardiac Troponin, and the amount of said natriuretic peptide to a reference amount for the natriuretic peptide, whereby atrial fibrillation is diagnosed.

The term "atrial fibrillation" is well known in the art. Atrial fibrillation is e.g. reviewed by Fuster et al. which herewith is incorporated by reference in its entire disclosure content (Fuster V, Rydén L E, Asinger R W, et al. ACC/AHA/ESC Guidelines for the Management of Patients With Atrial Fibrillation: Executive Summary A Report of the American College of Cardiology/American Heart Association Task Force on Practice Guidelines and the European Society of Cardiology Committee for Practice Guidelines and Policy Conferences (Committee to Develop Guidelines for the Management of Patients With Atrial Fibrillation) Developed in Collaboration With the North American Society of Pacing and Electrophysiology. Circulation. Oct. 23, 2001; 104(17):2118-50). Atrial fibrillation is an abnormal heart rhythm which involves the two upper chambers of the heart. In a normal heart rhythm, the impulse generated by the sino-atrial node spreads through the heart and causes contraction of the heart muscle and pumping of blood. In atrial fibrillation, the regular electrical impulses of the sino-atrial node are replaced by disorganized, rapid electrical impulses which result in irregular heart beats.

Atrial fibrillation (AF) can be permanent, persistent or intermittent (for an explanation of these terms, see also Fuster et al. (loc. cit.).

A subject, preferably, suffers from permanent AF, if the AF has persisted for more than one year. In particular, conversion back to sinus rhythm does not occur (or only if treated).

A subject, preferably, suffers from persistent AF, if the AF lasts more than 7 days and may require either pharmacologic or electrical intervention to terminate atrial fibrillation. Thus persistent AF occurs in episodes, but the arrhythmia does not convert back to sinus rhythm spontaneously.

A subject, preferably, suffers from intermittent AF (frequently also referred to as paroxymal AF), if there are episodes of atrial fibrillation that terminate spontaneously. The episodes of atrial fibrillation may last from seconds to days. Preferably, the episodes last less than one hour.

In the context of the aforementioned method, preferably, intermittent atrial fibrillation is diagnosed.

Permanent and persistent atrial fibrillation can be easily diagnosed, e.g., on an electrocardiogram. Characteristic findings are, preferably, the absence of P waves, unorganized electrical activity in their place, and irregularity of R-R interval due to irregular conduction of impulses to the ventricles. Intermittent atrial fibrillation is more difficult to diagnose, since a diagnosis is only possible during the episode of atrial fibrillation.

The inventors have surprisingly found that the determination of a cardiac Troponin (and, optionally of natriuretic peptide) in a sample of a subject suspected to suffer from atrial fibrillation allows for the diagnosis of atrial fibrillation. In particular, increased levels of a cardiac Troponin are indicative for a subject suffering AF, whereas decreased levels of a cardiac Troponin are indicative for a subject not suffering from AF. Further, the determination of a cardiac Troponin also allows for the diagnosis of intermittent AF, even in the absence of an episode of AF (at the time point at which the sample is obtained). Thus, by carrying out the aforementioned method, intermittent atrial fibrillation is, preferably, diagnosed in the absence of an episode of atrial fibrillation, in particular at the time point at which the sample is obtained. Thus, the subject, preferably, does not suffer from an episode of AF when the sample is obtained.

The subject in accordance with the aforementioned method of the present disclosure shall be suspected to suffer from atrial fibrillation. A subject suspected to suffer from atrial fibrillation (e.g. from intermittent atrial fibrillation), preferably, is a subject who has one or more risk factors of atrial fibrillation. These risk factors are well known in the art and include heart disease, including valve problems and a history of heart attack and heart surgery, systemic hypertension, especially if it's not well controlled with lifestyle changes or medications, and alcohol consumption. Preferably, the subject being suspected to belongs to a risk group. In particular, it is envisaged that the subject is a subject with proven or suspected cardiac disorders including subjects having risk factors predisposing to cardiac disorders such as arterial or systemic hypertension, diabetes mellitus, smokers, individuals with hyperlipemia or signs of the metabolic syndrome, in particular if the subject is at advanced age (more than 60, 65, 70 and preferably 75 years of age). Alternatively, or additionally the subject may, preferably, suffer from valvular disorders, preferably from mitral valve disorders. It is further envisaged that the subject suspected to suffer from AF, suffers from hyperthyroidism.

In some embodiments of the method of the present disclosure, the subject who is suspected to suffer from atrial fibrillation, preferably, suffers from ischemic stroke, in particular from cardioembolic ischemic stroke (for an explanation of the these terms, see elsewhere herein). If the subject to be tested in accordance with the aforementioned method suffers from ischemic stroke, the sample is, preferably, obtained immediately after the onset of stroke symptoms as described in the context of the method for early differentiating whether a subject suffers from cardioembolic stroke or from non-cardioembolic ischemic stroke.

However, it is also preferred that the subject to be tested does not suffer from ischemic stroke.

Preferably, the reference amount in connection with the aforementioned method is derived from a subject known to suffer from atrial fibrillation (or from a group of subjects), and wherein an identical amount of the cardiac Troponin (and, optionally, of the natriuretic peptide), or an amount of the cardiac Troponin (and, optionally, of the natriuretic peptide) which is increased as compared to the reference amount, indicates that the subject suffers from atrial fibrillation. Additionally or alternatively, the reference amount is derived from a subject known not to suffer from atrial fibrillation or from a group of such subjects, wherein an identical amount of the cardiac Troponin (and, optionally, of the natriuretic peptide), or an amount of the cardiac troponin Troponin (and, optionally, of the natriuretic peptide) which is decreased as compared to the reference amount, indicates that the subject does not suffer from atrial fibrillation.

Further, the reference amount may define a threshold amount for the cardiac Troponin (and, optionally for the natriuretic peptide), whereby an amount of Troponin (and, optionally of the natriuretic peptide) in the sample of the test subject larger than the respective threshold shall be indicative for atrial fibrillation, while an amount of Troponin (and, optionally, of the natriuretic peptide) in the sample of the test subject lower than the respective threshold shall indicate that the subject does not suffer from atrial fibrillation.

Exemplary reference amounts are indicated herein below.

A preferred reference amount indicating atrial fibrillation is an amount of a cardiac troponin, in particular of Troponin T of about 6 pg/ml to about 40 pg/ml and, more preferably, 8 to 30 pg/ml, or about 10 to about 20 pg/ml, even more preferably of about 15 to 20 pg/ml. Even more preferably, the reference is an amount of about 10 pg/ml, or most preferably, about 7 pg/ml. A test amount being essentially identical or increased shall be indicative for atrial fibrillation while a decreased amount in the test sample as compared to the reference amount shall indicate that the subject does not suffer from atrial fibrillation. Preferably, the aforementioned reference amounts are derived from a subject or a group of subjects known to suffer from atrial fibrillation.

An exemplary reference amount indicating atrial fibrillation is an amount of a natriuretic peptide, in particular, of NT-proBNP of about 300 pg/ml to about 1500 pg/ml and, more preferably, 400 to 1300 pg/ml, even more preferably of about 500 to 1000 pg/ml. Even more preferably, the reference is an amount of about 500, 400, or most preferably, of about 300 pg/ml. A test amount being essentially identical or increased shall be indicative for atrial fibrillation while a decreased amount in the test sample as compared to the reference amount shall indicate that the subject does not suffer from atrial fibrillation. Preferably, the aforementioned reference amounts are derived from a subject or a group of subjects known to suffer from atrial fibrillation.

As set forth above, the diagnosis of intermittent atrial fibrillation is challenging, whereas the diagnosis of permanent or persistent atrial fibrillation is rather easy. Since subjects with permanent and persistent atrial fibrillation can be identified without further ado, it is of particular interest to identify those subjects who do not suffer from permanent or persistent atrial fibrillation, but who suffer from intermittent atrial fibrillation.

Interestingly, it has been shown in the context of the studies of the present disclosure, that the levels of cardiac troponins and of natriuretic peptides are lower in subjects with intermittent atrial fibrillation than in subjects with persistent or permanent atrial fibrillation. This is advantageous, since the determination of a cardiac Troponin and, optionally, a natriuretic peptide allows to identify those patients who suffer from intermittent fibrillation.

Therefore, in a preferred embodiment of the present disclosure intermittent atrial fibrillation shall be diagnosed, in particular in subject suspected to suffer from intermittent atrial fibrillation.

In order to allow for the diagnosis of intermittent AF, the amount of the cardiac Troponin, and, optionally, the amount of the natriuretic peptide, as determined in step a) shall be compared in step b) to two reference amounts. It is envisaged that a first reference amount is derived from a subject known to suffer from intermittent AF (or from a group of such subjects), and that a second reference amount is derived from a subject known to suffer from permanent or, in particular, from persistent AF (or from a group of such subjects). Of course, the reference amounts shall be derived from samples of the aforementioned subjects.

Preferably, an amount of the cardiac Troponin and, optionally, of the natriuretic peptide in the sample of the test subject which is essentially identical or larger than the than the reference amount (for the cardiac Troponin and, optionally, for the natriuretic peptide) derived from a subject known to suffer from intermittent AF (or from a group of such subjects), but which is lower than the reference amount derived from a subject known to suffer from permanent or from persistent AF (or from a group of such subjects) is indicative for the diagnosis of intermittent AF.

A preferred reference amount for a cardiac Troponin, in particular for Troponin T, derived from a subject known to suffer from intermittent AF (or from a group of such subjects) is within a range of about 5 to 10 pg/ml. Preferably, the reference amount is about 9 pg/ml.

A preferred reference amount for a cardiac Troponin, in particular for Troponin T, derived from a subject known to suffer from permanent or from persistent AF (or from a group of such subjects) is within a range of about 12 to 25 pg/ml. Preferably, the reference amount is about 18 pg/ml.

A preferred reference amount for a natriuretic peptide, in particular for NT-proBNP, derived from a subject known to suffer from intermittent AF (or from a group of such subjects) is within a range of about 300 to 500 pg/ml. Preferably, the reference amount is about 350 pg/ml.

A preferred reference amount for a natriuretic peptide, in particular for NT-proBNP, derived from a subject known to suffer from permanent or from persistent AF (or from a group of such subjects) is within a range of about 900 to 1500 pg/ml. Preferably, the reference amount is about 900 pg/ml.

In another preferred embodiment of the method of diagnosing AF, intermittent AF is diagnosed. The subject according to this preferred embodiment shall be known not to suffer from permanent and/or persistent atrial fibrillation (which can be determined without further ado, see above).

Thus also envisaged is method for diagnosing intermittent atrial fibrillation in a subject suspected to suffer from intermittent atrial fibrillation, but known not to suffer from persistent and/or permanent atrial fibrillation, comprising
  a) determining the amount of a cardiac Troponin (and, optionally, a natriuretic peptide) in a sample from said subject, and
  b) comparing the, thus, determined amount of said cardiac Troponin (and, optionally of said natriuretic peptide) to a reference amount (s), whereby intermittent atrial fibrillation is diagnosed.

The subject suspected to suffer from intermittent AF, preferably, has the same risk factors as the subject suspected to suffer from AF (see elsewhere herein). In particular, it is envisaged that the subject suffers from ischemic stroke, in particular from cardioembolic ischemic stroke.

The reference amount to be applied in the context of the present disclosure shall be derived from a subject known to suffer from intermittent AF, or from a subject known not to suffer from AF.

Preferably, the reference amount in connection with the aforementioned embodiment is derived from a subject known to suffer from intermittent atrial fibrillation (or from a group of subjects), and wherein an identical amount of the cardiac Troponin (and, optionally, of the natriuretic peptide), or an amount of the cardiac Troponin (and, optionally, of the natriuretic peptide) which is increased as compared to the reference amount, indicates that the subject suffers intermittent atrial fibrillation. Additionally or alternatively, the reference amount is derived from a subject known not to suffer from atrial fibrillation, wherein an identical amount of the cardiac Troponin (and, optionally, of the natriuretic peptide), or an amount of the cardiac troponin Troponin (and, optionally, of the natriuretic peptide) which is decreased as compared to the reference amount, indicates that subject does not suffer from intermittent atrial fibrillation.

A preferred reference amount indicating intermittent atrial fibrillation is an amount of a cardiac troponin, in particular of Troponin T of about 5 pg/ml to about 30 pg/ml and, more preferably, 5 to 25 pg/ml, or about 6 to about 10 pg/ml, even more preferably of about 6 to 8 pg/ml. Even more preferably, the reference is an amount of about 8 pg/ml, or most preferably, about 7 pg/ml. A test amount being essentially identical or increased shall be indicative for intermittent atrial fibrillation while a decreased amount in the test sample as compared to the reference amount shall indicate that the subject does not suffer from intermittent atrial fibrillation. Preferably, the aforementioned reference amounts are derived from a subject or a group of subjects known to suffer from intermittent atrial fibrillation.

A preferred reference amount indicating intermittent atrial fibrillation is an amount of a natriuretic peptide, in particular, of NT-proBNP of about 300 pg/ml to about 800 pg/ml and, more preferably, 300 to 700 pg/ml, even more preferably of about 350 to 500 pg/ml. Even more preferably, the reference is an amount of about 500, 400, or most preferably, of about 300 pg/ml. A test amount being essentially identical or increased shall be indicative for intermittent atrial fibrillation while a decreased amount in the test sample as compared to the reference amount shall indicate that the subject does not suffer from intermittent atrial fibrillation. Preferably, the aforementioned reference amounts are derived from a subject or a group of subjects known to suffer from intermittent atrial fibrillation.

In a preferred embodiment of the aforementioned method of the present disclosure, said method further comprises recommending a therapy for said subject, if the subject has been diagnosed to suffer atrial fibrillation, in particular from intermittent atrial fibrillation. Preferred therapies that can be recommended in a subject who suffers from atrial fibrillation are, e.g., described by Fuster et al. (Fuster et al. J Am Coll Cardiol 2001: 38: 1231, and Fuster V. et al. Circulation 2006: 114 to 257). Preferred therapies included, administration of beta blockers, non-dihydropyridine calcium channel blockers, digoxin, vitamin K antatgonists, aspirin, acetylsalicylic acid. Moreover, pharmacologic or electrical intervention can be recommended to terminate atrial fibrillation. Pharmacologic intervention, preferably, include administration of flecainide, dofetilide, propafenone and/or ibutilide. Further envisaged is the administration of factor Xa inhibitors such as rivaroxoban and/or dabigatran (see Patel M. R. et al, NEJM 2011: 365: 883-91; Connolly S. J. et al NEJM 2010: 261: 1139-51).

Preferred embodiments of the aforementioned method.

Preferably, intermittent atrial fibrillation is diagnosed.

In a preferred embodiment, the subject does not suffer from ischemic stroke.

In another preferred embodiment, the subject suspected to suffer from atrial fibrillation suffers from ischemic stroke, in particular from cardioembolic stroke, and wherein the sample has been obtained immediately after the onset of symptoms of ischemic stroke. Preferably, the sample from said subject has been obtained from said subject not more than 12 hours after the onset of symptoms of ischemic stroke, in particular not more than 6 hours or not more than 3 hours after the onset of symptoms of ischemic stroke.

In a preferred embodiment, wherein the subject is known not to suffer from persistent and/or permanent atrial fibrillation, in particular, wherein the reference amount is derived from a subject known to suffer from intermittent atrial fibrillation or from a group of such subjects, and wherein an identical amount of the cardiac Troponin, or an amount of the cardiac Troponin which is increased as compared to the reference amount, indicates that the subject suffers intermittent atrial fibrillation, and/or wherein the reference amount is derived from a subject known not to suffer from atrial fibrillation or from a group of such subjects, wherein an identical amount of the cardiac Troponin, or an amount of the cardiac troponin Troponin which is decreased as compared to the reference amount, indicates that subject does not suffer from intermittent atrial fibrillation.

In another preferred embodiment, the amount of the cardiac Troponin in the sample from the subject is compared to two reference amounts, wherein the first reference amount is derived from a subject known to suffer from intermittent AF or from a group of such subjects, and wherein the second reference amount is derived from a subject known to suffer from permanent or from persistent AF or from a group of such subjects. Preferably, an amount of the cardiac Troponin in the sample of the subject which is essentially identical or larger than the than the first reference amount, but which is lower than the second reference amount derived from a subject known to suffer from permanent or from persistent AF is indicative for the diagnosis of intermittent AF.

In a preferred embodiment, the method further comprises the determination of the amount of a natriuretic peptide, in particular of a brain natriuretic peptide, in particular of BNP and NT-proBNP.

Preferably, intermittent atrial fibrillation is diagnosed in the absence of an episode of atrial fibrillation, in particular at the time point at which the sample is obtained.

In another aspect of the disclosure, a system for diagnosing AF, in particular, intermittent AF, is contemplated, comprising:

a) an analyzer unit configured to bringing a sample from a subject who is suspected to suffer from AF, in particular, intermittent AF into contact with a detection agent that specifically binds to the marker cardiac Troponin for a time sufficient to allow for the formation of a complex of the said detection agent and the marker from the sample, b) an analyzer unit configured to measure the amount of the formed complex, wherein the said amount of the formed complex is proportional to the amount of the marker present in the sample, c) a computing device having a processor and in operable communication with said analysis units, and d) a non-transient machine readable media including a plurality of instructions executable by the processor, the instructions, when executed transform the amount of the formed complex into an amount of the marker reflecting the amount of the marker present in the sample, compare said amount to a reference, and establish an aid for diagnosing AF, in particular, intermittent AF based on the result of said comparison to said reference.

Preferably, the system also comprises a detection agent that specifically binds to natriuretic peptide.

In yet an aspect of the aforementioned method, step a) may be carried out by an analyzer unit, in an aspect, an analyzer unit as defined elsewhere herein.

In an aspect of the method of the disclosure, the amount determined in step a) is compared to a reference. In an aspect, the reference is a reference as defined elsewhere herein. In yet another aspect, the reference takes into account the proportional relationship between the measured amount of complex and the amount present in the original sample. Thus, the references applied in an aspect of the method of the disclosure are artificial references which are adopted to reflect the limitations of the detection agent that has been used. In another aspect, said relationship can be also taken into account when carrying out the comparison, e.g., by including a normalization and/or correction calculation step for the determined amount prior to actually comparing the value of the determined amount and the reference. Again, the normalization and/or correction calculation step for the determined amount adopts the comparison step such that the limitations of the detection agent that has been used are reflected properly. In an aspect, the comparison is carried out automatically, e.g., assisted by a computer system or the like.

The aid for diagnosing AF, in particular, intermittent AF is established based on the comparison carried out in step b) by allocating the subject either (i) the group of subjects who suffer from AF or (ii) the group of who do not suffer from AF as set forth herein elsewhere. As discussed elsewhere herein already, the allocation of the investigated subject must not be correct in 100% of the investigated cases. Moreover, the groups of subjects into which the investigated subject is allocated are artificial groups in that they are established based on statistical considerations, i.e. a certain preselected degree of likelihood based on which the method of the disclosure shall operate. In an aspect of the disclosure, the aid for optimizing a risk assessment is established automatically, e.g., assisted by a computing device or the like, as described and disclosed herein.

In an aspect of the method of the disclosure, said method further comprises a step of recommending and/or managing the subject according to the result established in step c) as set forth elsewhere herein in detail.

In an aspect of the aforementioned method, steps b) and/or c) are carried out by one or more analyzer units as set forth elsewhere herein.

Moreover, the present disclosure relates to the use of a cardiac Troponin and/or of a detection agent, which specifically binds thereto (and optionally of a natriuretic peptide and/or of detection agent, which specifically binds thereto) in a sample of a subject suffering from ischemic stroke for early differentiating whether the subject suffers from cardioembolic ischemic stroke or from non-cardioembolic ischemic stroke, wherein the sample has been obtained immediately after the onset of symptoms of ischemic stroke. Preferably, said sample has been obtained not more than 6 hours after the onset of symptoms of stroke.

Also envisaged by the present disclosure is the use of a cardiac Troponin and/or of a detection agent, which specifically binds thereto (and optionally of a natriuretic peptide and/or of detection agent, which specifically binds thereto) in a sample of a subject suspected to suffer from atrial fibrillation for diagnosing atrial fibrillation in a said subject. Preferably, intermittent atrial fibrillation is diagnosed.

The term "detection agent" as used herein refers to an agent which is capable of specifically recognizing and binding the biomarker referred to herein (a cardiac Troponin, or a natriuretic peptide) when present in a sample. Moreover, said agent shall allow for direct or indirect detection of the complex formed by the said agent and the biomarker. Direct detection can be achieved by including into the agent a detectable label. Indirect labelling may be achieved by a further agent which specifically binds to the complex comprising the biomarker and the detection agent wherein the said further agent is than capable of generating a detectable signal. Suitable compounds which can be used as detection agents are well known in the art. Preferably, the detection agent is an antibody or aptamere which specifically binds to the biomarker. Antibodies as referred to herein include both polyclonal and monoclonal antibodies, as well as fragments thereof, such as Fv, Fab and $F(ab)_2$ fragments that are capable of binding antigen or hapten. Also envisaged are single chain antibodies and humanized hybrid antibodies wherein amino acid sequences of a non-human donor antibody exhibiting a desired antigen-specificity are combined with sequences of a human acceptor antibody.

The present disclosure further relates to a device for early differentiating whether a subject suffers from cardioembolic ischemic stroke or from non-cardioembolic ischemic stroke in a subject suffering from ischemic stroke, said device comprising:

a) an analyzing unit (or an analyzer unit) comprising a detection agent for a cardiac Troponin which allows for the determination of the amount of said cardiac Troponin (and, optionally, a detection agent for a natriuretic peptide which allows for the determination of the amount of said natriuretic peptide); and b) an evaluation unit (or an analyzer unit) comprising a data processor having implemented an algorithm for comparing the amount(s) determined by the analyzing unit with reference amount(s) stored in a database in order to differentiate whether a subject suffers from cardioembolic ischemic stroke or from non-cardioembolic ischemic stroke, wherein the reference amount is derived from a sample from a reference subject as described herein elsewhere in the context of the method for differentiating whether a subject suffers from cardioembolic ischemic stroke or from non-cardioembolic ischemic stroke, and the algorithm is an algorithm as defined in the context of the said method.

The present disclosure further relates to a device for diagnosing atrial fibrillation, in particular, intermittent atrial fibrillation in a subject suspected to suffer from atrial fibrillation, said device comprising:

a) an analyzing unit (or an analyzer unit) comprising a detection agent for a cardiac Troponin which allows for the determination of the amount of said cardiac Troponin (and, optionally, a detection agent for a natriuretic peptide which allows for the determination of the amount of said natriuretic peptide); and b) an evaluation unit (or an analyzer unit) comprising a data processor having implemented an algorithm for comparing the amount(s) determined by the analyzing unit with reference amount(s) stored in a database in order to diagnose atrial fibrillation, in particular intermittent atrial fibrillation, wherein the reference amount is derived from a sample from a reference subject as described herein elsewhere in the context of the method for diagnosing atrial fibrillation (in particular, intermittent atrial fibrillation), and the algorithm is an algorithm as defined in the context of the method for diagnosing atrial fibrillation (in particular atrial fibrillation).

The term "device" as used herein relates to a system comprising the aforementioned units operatively linked to each other as to allow the diagnosis according to the methods of the disclosure. Preferred detection agents which can be used for the analyzing unit are disclosed elsewhere herein. The analyzing unit, preferably, comprises said detection agents in immobilized form on a solid support which is to be contacted to the sample comprising the biomarkers the amount of which is to be determined. Moreover, the analyzing unit can also comprise a detector which determines the amount of detection agent which is specifically bound to the biomarker(s). The determined amount can be transmitted to the evaluation unit. Said evaluation unit comprises a data processing element, such as a computer, with an implemented algorithm for carrying out a comparison between the determined amount and a suitable reference. Suitable references can be derived from samples of subjects to be used for the generation of reference amounts as described elsewhere herein above. The diagnostic results may be given as output of parametric diagnostic raw data, preferably, as absolute or relative amounts. It is to be understood that these data may need interpretation by the clinician. However, also envisage are expert system devices wherein the output comprises processed diagnostic raw data the interpretation of which does not require a specialized clinician. Preferably, the device of the present disclosure can be used to carry out the aforementioned method of the present disclosure in an automated manner.

A preferred embodiment of the instant disclosure includes a system for guiding exercise as set forth herein. Examples of systems include clinical chemistry analyzers, coagulation chemistry analyzers, immunochemistry analyzers, urine analyzers, nucleic acid analyzers, used to detect the result of chemical or biological reactions or to monitor the progress of chemical or biological reactions. More specifically, exemplary systems of the instant disclosure may include Roche Elecsys™ Systems and Cobas® e Immunoassay Analyzers, Abbott Architect™ and Axsym™ Analyzers, Siemens Centaur™ and Immulite™ Analyzers, and Beckman Coulter UniCel™ and Acess™ Analyzers, or the like.

Embodiments of the system may include one or more analyzer units utilized for practicing the subject disclosure. The analyzer units of the system disclosed herein are in operable communication with the computing device disclosed herein through any of a wired connection, Bluetooth, LANS, or wireless signal, as are known. Additionally, according to the instant disclosure, an analyzer unit may comprise a stand-alone apparatus, or module within a larger instrument, which performs one or both of the detection, e.g. qualitative and/or quantitative evaluation of samples for diagnostic purpose. For example, an analyzer unit may perform or assist with the pipetting, dosing, mixing of samples and/or reagents. An analyzer unit may comprise a reagent holding unit for holding reagents to perform the assays. Reagents may be arranged for example in the form of containers or cassettes containing individual reagents or group of reagents, placed in appropriate receptacles or positions within a storage compartment or conveyor. Detection reagents may also be in immobilized form on a solid support which are contacted with the sample. Further, an analyzer unit may include a process and/or detection component which is optimizable for specific analysis.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electromagnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable pre-preamplifiers include, for example, integrating, transimpedance, and current gain (current mirror) preamplifiers.

Additionally, one or more analyzer unit according to the instant disclosure may comprise a light source for emitting light. For example, a light source of an analyzer unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme).

Further, an analyzer unit of the system may include one or more incubation units (for example, for maintaining a sample or a reagent at a specified temperature or temperature range). In some embodiments, an analyzer unit may include a thermocycler, include a real-time thermocycler, for subjecting a sample to repeated temperature cycles and monitoring a change in the amount of an amplification product with the sample.

Additionally, an analyzer unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposable pipette tips. The analyzer unit may further comprise one or more mixing units, for example a shaker to shake a cuvette comprising a liquid, or a mixing paddle to mix liquids in a cuvette, or reagent container.

It follows from the above that according to some embodiments of the instant disclosure, portions of some steps of methods disclosed and described herein may be performed by a computing device. A computing device may be a general purpose computer or a portable computing device, for example. It should also be understood that multiple computing devices may be used together, such as over a network or other methods of transferring data, for performing one or more steps of the methods disclosed herein. Exemplary computing devices include desktop computers, laptop computers, personal data assistants ("PDA"), such as BLACKBERRY brand devices, cellular devices, tablet computers, servers, and the like. In general, a computing device comprises a processor capable of executing a plurality of instructions (such as a program of software).

A computing device has access to a memory. A memory is a computer readable medium and may comprise a single storage device or multiple storage devices, located either locally with the computing device or accessible to the computing device across a network, for example. Computer-readable media may be any available media that can be accessed by the computing device and includes both volatile and non-volatile media. Further, computer readable-media may be one or both of removable and non-removable media.

By way of example, and not limitation, computer-readable media may comprise computer storage media. Exemplary computer storage media includes, but is not limited to, RAM, ROM, EEPROM, flash memory or any other memory technology, CD-ROM, Digital Versatile Disk (DVD) or other optical disk storage, magnetic cassettes, magnetic tape, magnetic disk storage or other magnetic storage devices, or any other medium which can be used for storing a plurality of instructions capable of being accessed by the computing device and executed by the processor of the computing device.

According to embodiments of the instant disclosure, software may include instructions which, when executed by a processor of the computing device, may perform one or more steps of the methods disclosed herein. Some of the instructions may be adapted to produce signals that control operation of other machines and thus may operate through those control signals to transform materials far removed from the computer itself. These descriptions and representations are the means used by those skilled in the art of data processing, for example, to most effectively convey the substance of their work to others skilled in the art.

The plurality of instructions may also comprise an algorithm which is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as values, characters, display data, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities. According to some embodiments of the instant disclosure, an algorithm for carrying out a comparison between a determined amount of one or more markers disclosed herein, and a suitable reference, is embodied and performed by executing the instructions. The results may be given as output of parametric diagnostic raw data or as absolute or relative amounts. According to various embodiments of the system disclosed herein, a "diagnosis" may be provided by the computing device of a system disclosed herein based on said comparison of the calculated "amount" to a reference or a threshold. For example, a computing device of a system may provide an indicator, in the form of a word, symbol, or numerical value which is indicative of a particular diagnosis.

The computing device may also have access to an output device. Exemplary output devices include fax machines, displays, printers, and files, for example. According to some embodiments of the present disclosure, a computing device may perform one or more steps of a method disclosed herein, and thereafter provide an output, via an output device, relating to a result, indication, ratio or other factor of the method.

The present disclosure further encompasses a kit for early differentiating whether a subject suffers from cardioembolic ischemic stroke or from non-cardioembolic ischemic stroke in a subject suffers from ischemic stroke, said kit comprising a detection agent for a cardiac Troponin and a standard (standards) which reflects the reference amount(s) as derived from a sample from a subject known suffer from cardioembolic stroke and/or from a subject known to suffer from non-cardioembolic stroke.

The present disclosure, finally, encompasses a kit for diagnosing atrial fibrillation in a subject suspected to suffer from atrial fibrillation, said kit comprising a detection agent for a cardiac Troponin (and, optionally, for a natriuretic peptide) and a standard (standards) which reflects the reference amount(s) as derived from a sample from a subject known suffer from atrial fibrillation and/or from a subject known not to suffer from atrial fibrillation.

The term "kit" as used herein refers to a collection of the aforementioned components, preferably, provided in separately or within a single container. The container also comprises instructions for carrying out the method of the present disclosure. These instructions may be in the form of a manual or may be provided by a computer program code which is capable of carrying out the comparisons referred to in the methods of the present disclosure and to establish a diagnosis accordingly when implemented on a computer or a data processing device. The computer program code may be provided on a data storage medium or device such as a optical storage medium (e.g., a Compact Disc) or directly on a computer or data processing device. Moreover, the kit may, preferably, comprise standards which reflect the reference amounts as described and referred to elsewhere herein in detail. The detection agent is, preferably, immobilized on a carrier, and, preferably, a test stripe The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

ILLUSTRATIVE EMBODIMENTS

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A method for early differentiating whether a subject suffers from cardioembolic ischemic stroke or from non-cardioembolic ischemic stroke, comprising determining the amount of a cardiac Troponin in a sample from a subject suffering from ischemic stroke, wherein the sample has been obtained not more than 6 hours after the onset of symptoms of ischemic stroke.
2. The method of embodiment 1, further comprising the step of comparing the amount of said cardiac Troponin to a reference amount, thereby differentiating whether said subject suffers from cardioembolic stroke or from non-cardioembolic ischemic stroke.
3. The method of embodiments 1 and 2, wherein the sample been obtained from said subject not more than 3 hours after the onset of symptoms of ischemic stroke.
4. The method of any one of embodiments 1 to 3, wherein the reference amount is derived from a subject known to suffer from cardioembolic stroke, and wherein an identical amount of the cardiac Troponin, or an amount of the cardiac troponin which is increased as compared to the reference amount, indicates that the subject suffers from cardioembolic stroke, and/or wherein the reference amount is derived from a subject known to suffer from non-cardioembolic ischemic stroke, and wherein an identical amount of the cardiac Troponin, or an amount of the cardiac troponin which is decreased as compared to the reference amount, indicates that the subject suffers from non-cardioembolic ischemic stroke.

5. The method of any one of embodiments 1 to 5, further comprising the determination of the amount of a natriuretic peptide, in particular of a brain natriuretic peptide, in particular of BNP or NT-proBNP.

6. Use of a cardiac Troponin and/or of a detection agent, which specifically binds thereto in a sample of a subject for early differentiating whether the subject suffers from cardioembolic ischemic stroke or from non-cardioembolic ischemic stroke, wherein the sample has been obtained not later than 6 hours after the onset of symptoms of ischemic stroke.

7. A device for early differentiating whether a subject suffers from cardioembolic ischemic stroke or from non-cardioembolic ischemic stroke in a subject suffering from ischemic stroke, said device comprising:
    a) an analyzing unit comprising a detection agent for a cardiac Troponin which allows for the determination of the amount of said cardiac Troponin (and, optionally, a detection agent for a natriuretic peptide which allows for the determination of the amount of said natriuretic peptide); and
    b) an evaluation unit comprising a data processor having implemented an algorithm for comparing the amount(s) determined by the analyzing unit with reference amount(s) stored in a database in order to differentiate whether a subject suffers from cardioembolic ischemic stroke or from non-cardioembolic ischemic stroke, wherein the reference amount is derived from a sample from a subject known to suffer from cardioembolic stroke and/or from a sample from a subject known to suffer from non-cardioembolic ischemic stroke, wherein said sample has been obtained not more than 6 hours after the onset of symptoms of ischemic stroke, and wherein the algorithm is as follows:
        i) an identical amount of the cardiac Troponin, or an amount of the cardiac troponin which is increased as compared to the reference amount, is indicative for a subject suffers from cardioembolic stroke, if the reference amount is derived from a subject known to suffer from cardioembolic stroke, and/or
        ii) an identical amount of the cardiac Troponin, or an amount of the cardiac troponin which is decreased as compared to the reference amount, is indicative for a subject who suffers from non-cardioembolic ischemic stroke, if the reference amount is derived from a subject known to suffer from non-cardioembolic ischemic stroke.

8. A method for diagnosing intermittent atrial fibrillation in a human subject suspected to suffer from atrial fibrillation, comprising determining the amount of a cardiac Troponin in a sample from said subject.

9. The method of embodiment 8, further comprising the step of comparing the amount of the cardiac Troponin to a reference amount.

10. The method of embodiments 8 and 9, wherein the subject does not suffer from ischemic stroke.

11. The method of embodiments 8 and 9, wherein the subject suspected to suffer from atrial fibrillation suffers from ischemic stroke, in particular from cardioembolic stroke, and wherein the sample has been obtained immediately after the onset of symptoms of ischemic stroke.

12. The method of embodiment 11, wherein said sample from said subject has been obtained from said subject not more than 12 hours after the onset of symptoms of ischemic stroke, in particular not more than 6 hours or not more than 3 hours after the onset of symptoms of ischemic stroke.

13. The method of embodiments 8 to 12, wherein the subject is known not to suffer from persistent and permanent atrial fibrillation.

14. The method of embodiment 13, wherein the reference amount is derived from a subject known to suffer from intermittent atrial fibrillation or from a group of such subjects, and wherein an identical amount of the cardiac Troponin, or an amount of the cardiac Troponin which is increased as compared to the reference amount, indicates that the subject suffers intermittent atrial fibrillation, and/or wherein the reference amount is derived from a subject known not to suffer from atrial fibrillation or from a group of such subjects, wherein an identical amount of the cardiac Troponin, or an amount of the cardiac troponin Troponin which is decreased as compared to the reference amount, indicates that subject does not suffer from intermittent atrial fibrillation.

15. The method of embodiments 9 to 12, wherein the amount of the cardiac Troponin in the sample from the subject is compared to two reference amounts, wherein the first reference amount is derived from a subject known to suffer from intermittent AF or from a group of such subjects, and wherein the second reference amount is derived from a subject known to suffer from permanent or from persistent AF or from a group of such subjects.

16. The method of embodiment 15, wherein an amount of the cardiac Troponin in the sample of the subject which is essentially identical or larger than the than the first reference amount, but which is lower than the second reference amount derived from a subject known to suffer from permanent or from persistent AF is indicative for the diagnosis of intermittent AF.

17. The method of any one of embodiments 8 to 16, further comprising the determination of the amount of a natriuretic peptide, in particular of a brain natriuretic peptide, in particular of BNP and NT-proBNP.

18. The method of any one of embodiments 8 to 17, wherein intermittent atrial fibrillation is diagnosed in the absence of an episode of atrial fibrillation, in particular at the time point at which the sample is obtained.

19. Use of a cardiac Troponin and/or of a detection agent, which specifically binds thereto in a sample of a subject for early differentiating whether the subject suffers from cardioembolic ischemic stroke or from non-cardioembolic ischemic stroke, wherein the sample has been obtained not later than 6 hours after the onset of symptoms of ischemic stroke.

20. Use of a cardiac Troponin and/or of a detection agent, which specifically binds thereto in a sample of a human subject suspected to suffer from atrial fibrillation for diagnosing intermittent atrial fibrillation in a said subject.

21. A device for early differentiating whether a subject suffers from cardioembolic ischemic stroke or from non-cardioembolic ischemic stroke in a subject suffering from ischemic stroke, said device comprising:
   a) an analyzing unit comprising a detection agent for a cardiac Troponin which allows for the determination of the amount of said cardiac Troponin (and, optionally, a detection agent for a natriuretic peptide which allows for the determination of the amount of said natriuretic peptide); and
   b) an evaluation unit comprising a data processor having implemented an algorithm for comparing the amount(s) determined by the analyzing unit with reference amount(s) stored in a database in order to differentiate whether a subject suffers from cardioembolic ischemic stroke or from non-cardioembolic ischemic stroke, wherein the reference amount is derived from a sample from a subject defined in embodiment 4, and the algorithm is an algorithm as defined in embodiment 4.

22. A device for diagnosing intermittent atrial fibrillation in a subject suspected to suffer from atrial fibrillation, said device comprising:
   a) an analyzing unit comprising a detection agent for a cardiac Troponin which allows for the determination of the amount of said cardiac Troponin; and
   b) an evaluation unit comprising a data processor having implemented an algorithm for comparing the amount determined by the analyzing unit with a reference amount (or reference amounts) stored in a database in order to diagnose intermittent atrial fibrillation, wherein the reference amount is derived from a sample from a reference subject as defined in embodiment 14 or 15, and the algorithm is an algorithm as defined in embodiment 14 or 16.

EXAMPLES

Example 1: Determination of Troponin T, GDF-15 and NT-proBNP

Troponin T was determined using Roche's electrochemiluminescence ELISA sandwich test Elecsys Troponin T hs (high sensitive) STAT (Short Turn Around Time) assay. The test employs two monoclonal antibodies specifically directed against human cardiac troponin T. The antibodies recognize two epitopes (amino acid position 125-131 and 136-147) located in the central part of the cardiac troponin T protein, which consists of 288 amino acids (analytical sensitivity below 1.0).

NT-proBNP was determined using Roche's electrochemiluminescence ELISA sandwich test Elecsys proBNP II STAT (Short Turn Around Time) assay. The test employs two monoclonal antibodies which recognize epitopes located in the N-terminal part (1-76) of proBNP (1-108).

To determine the concentration of GDF-15 in serum and plasma samples, an Elecsys prototype test was employed, using a polyclonal, GDF-15 affinity chromatography-purified, goat anti-human GDF-15 IgG antibody from R&D Systems (AF957). In each experiment, a standard curve was generated with recombinant human GDF-15 from R&D Systems (957-GD/CF). The results with new batches or recombinant GDF-15 protein were tested in standard plasma samples and any deviation above 10% was corrected by introducing an adjustment factor for this assay. GDF-15 measurements in serum and plasma samples from the same patient yielded virtually identical results after correction for eventual dilution factors. The detection limit of the assay was 200 pg/ml.

Example 2: Patient Cohort

A total of 255 patients with ischemic stroke (mean age 70 years) were tested for NT pro BNP, trponinT and GDF 15. Transitory ischemic attack was present in 23 patients, minor stroke was diagnosed in 61 patients and major stroke was found in 108 patients. In addition as described above caotoid and transcranial ultrasound as well as electro- and echocardiography were performed and the patients were classified according to the TOAST criteria. Moreover a 7 day HOLTER ECG was performed to identify unnoticed atrial fibrillation on the routine electrocardiogram.

Example 3: Results

The following results were obtained (indicated are the median values, the 25. percentile and the 75. percentile):

|  | Troponin T pg/ml | NT-pro BNP pg/ml | GDF 15 pg/ml |
| --- | --- | --- | --- |
| Large Artery stenosis | 4.9 | 262 | 1146 |
| N = 46 | 0.0-16.3 | 110-611 | 801-1404 |
| Cardioembolic stroke | 11.6 | 868 | 1393 |
| N = 66 | 3.8-29 | 365-1863 | 1005-2481 |
| Small vessel | 6.3 | 222 | 1188 |
| N = 32 | 0.0-9.3 | 79-412 | 822-2025 |
| Undetermined | 5.3 | 152 | 1106 |
| N = 97 | 0.0-10.8 | 63-371 | 805-1522 |

As previously described cardioembolic stroke was associated with increased NT-pro BNP levels, GDF 15 did not contribute significantly to stroke classification, however sensitive troponin T did and thereby excluding the difficulties of separating cardiac and brain B type natriuretic peptides.

These data are further supported by the classification related to the presence of absence of atrial fibrillation. The results are as follows:

|  | Troponin T Pg/ml | N T-pro BNP pg/ml | GDF 15 pg/ml |
| --- | --- | --- | --- |
| Atrial fibrillation | 15.8 | 1773 | 2220 |
| N = 44 | 8-35 | 996-2667 | 1288-3069 |
| Intermittent AF | 9.2 | 448 | 1364 |
| N = 28 | 4.9-24 | 321-802 | 1120-2214 |
| No AF | 4.3 | 137 | 1069 |
| N = 101 | 0-10.6 | 62-386 | 765-1480 |

These data again demonstrate the association of AF with NT-pro BNP and tropinin T but to a much lower extent with GDF 15. The limitations of NT-pro BNP to be used in the classification were also supported by the fact that median NT-pro BNP levels increased from presentation (331 pg/ml) to 24 h follow up to 437 pg/ml, which is in the range of 30% increase. To what extent this increase was due to cardiac causes or released from the brain is not clear. In contrast, there was no significant increase of Troponin T in the follow-up. Thus, Troponin T levels remained stable.

In summary troponin T was found to be a powerful tool in the identification/separation of causes of stroke. This method can also be used in stroke prevention in combination with B type natriuretic peptides. GDF 15 provided surprisingly little additional information to this important clinical question.

Example 4: Case Studies

A 68 year old male is diagnosed with TIA (transient ischemic attack) based on clinical symptoms and a subsequent MRI. His ECG is normal. His troponin T is 10.2 pg/ml, his NT-pro BNP is 520 pg/ml. An echocardiogram shown mild left ventricular dysfunction, in the atria there was no thrombus formation. Based on the TOAST criteria, the subject diagnosed as cardioembolic stroke after ruling out other possibilities. Because of the intraatrial thrombus formation he receives a Holter ECG for 3 days which reveals paroxysmal atrial fibrillation. He is then places on anticoagulant therapy as he had no contraindications.

A 72 year old male presents with minor stroke confirmed by MRI after ruling out intracerebral bleeding by CT scan. His Troponin T is 4.1 pg/ml and his NT-pro BNP is 245 pg/ml. A Carotis ultrasound reveals a 80% stenosis of the right carotis fork. ECG and echocardiography are normal, except minor diastolic dysfunction. As he is unlikely to have AF a Holter ECG was not carried out. He is advised to consider revision of the obstructed carotis after more intense evaluation of intra- and extracerebral arteries.

A 52 year old female reports dizzyness and palpitations and visits the emergency room. Her Troponin T is 3 pg/ml, NT-pro BNP is 115 pg/ml, the ECG and the echocardiography are within normal. Because symptoms do not direct to a cerebral event or atrial fibrillation no further investigations were done which is in concordance with the troponin T and NT-pro BNP results. She was discharged with a suspected anxiety syndrome.

A 58 year male presents to the emergency room because of temporary weakness of his left arm. His ECG is normal, his Troponin T is 11.1 pg/ml and NT-pro BNP is 435 pg/ml. A MRI rules out stroke, because of the Troponin T and NT-pro BNP results a Holter ECG was later performed which revealed paroxysmal AF. A subsequent Echo including TTE revealed intraatrial thrombi. He is diagnosed with paroxysmal atrial fibrillation and put on anticoagulant therapy with no obvious contraindications.

A 58 year old male presents with an ischemic stroke 2 hours after start of symptoms to the emergency room, symptoms include sudden weakness of the right arm and leg, his Troponin T is 12.5 pg/ml and NT-pro BNP is 920 pg/ml. Suspected cardioembolic stroke is confirmed by esophageal echocardiography with a visible thrombus in the left atrium. Angiography associated with lysis therapy confirmed the diagnosis. Lysis therapy was successful and symptoms improved, the patient is placed on anticoagulants.

A 58 year old male presents with dizzyness to his doctor, he had diabetes mellitus for the past 8 years and he had smoked for the most time in this life, arterial hypertension was known for the past 10 years. Imaging excludes TIA, on echocardiography he has a dilatated left atrium without thrombus formation, at presentation his ECG is normal and sinus rhythm was recorded. His troponin is 11 pg/ml, NT-pro BNP is 480 pg/ml. A few weeks later, the patient is put on Holter ECG and intermittent atrial fibrillation is recorded.

CONCLUSIONS

The identification of stroke patients with cardioembolic stroke is of importance as it directs further diagnostic steps and treatment and even more importantly the prevention of future strokes. Natriuretic peptides have shown usefulness in detecting candidates for cardioembolic stroke in patients presenting with ischemic stroke. However, as shown here natriuretic peptides may change during the course of stroke limiting their diagnostic potential, this is not the case with troponin T which is not subject to substantial change.

A similar reasoning applies to the detection of paroxymal or intermittent atrial fibrillation. Atrial fibrillation is more frequent in the elderly population. Since diagnostic methods (Holter ECG and detections methods for resulting atrial thrombi, TEE) are of limited availability patient selection (rule in/rule out) is important. This can be achieved by the determination of troponin T (and NT-pro BNP) and the use of appropriate cut offs.

In conclusion the inventors have identified troponin T as an important diagnostic method in ischemic stroke as well as in intermittent atrial fibrillation in order to direct further diagnostic methods and treatment schedules.

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method of diagnosing intermittent atrial fibrillation in a human patient suspected of having intermittent atrial fibrillation, the method comprising the steps of:
   contacting, in vitro, a portion of a plasma or serum sample obtained from the human patient with a binding agent comprising an antibody or antigen-binding fragment thereof that specifically binds Troponin T, said binding agent having a detectable label, whereby a complex of the binding agent and the Troponin T is formed;
   separating the complex from binding agent and sample not comprising the complex;
   measuring the amount of complex separated in said step of separating by detecting the presence of the detectable label, whereby a concentration of the Troponin T in the sample is calculated;
   comparing the concentration of the Troponin T in the sample to a first Troponin reference concentration and a second Troponin reference concentration, the second Troponin reference concentration being greater than the first Troponin reference concentration and determining that the concentration of Troponin T from the patient is greater than the first Troponin reference concentration and less than the second Troponin reference concentration; and
   Administering a compound to the patient after determining that the concentration of Troponin T from the patient is greater than the first Troponin reference concentration and less than the second Troponin reference concentration, wherein the compound is selected from the group consisting of a beta-blocker, a non-dihydropyridine calcium channel blocker, a digoxin, a vitamin K antagonist, acetylsalicylic acid and a factor Xa inhibitor.

2. The method of claim 1, wherein the patient also has ischemic stroke.

3. The method of claim 2 wherein the sample is obtained immediately after the onset of symptoms of ischemic stroke.

4. The method of claim 2 wherein the sample is obtained not more than 12 hours after the onset of symptoms of ischemic stroke.

5. A method of diagnosing intermittent atrial fibrillation in a human patient suspected of having intermittent atrial fibrillation, the method comprising the steps of:
   contacting, in vitro, a portion of a plasma or serum sample obtained from the human patient with a binding agent comprising an antibody or antigen-binding fragment thereof that specifically binds Troponin T, said binding agent having a detectable label, whereby a complex of the binding agent and the Troponin T is formed;
   separating the complex from binding agent and sample not comprising the complex;
   measuring the amount of complex separated in said step of separating by detecting the presence of the detectable label, whereby a concentration of the Troponin T in the sample is calculated;
   comparing the concentration of the Troponin T in the sample to a first Troponin reference concentration and a second Troponin reference concentration, the second Troponin reference concentration being greater than the first Troponin reference concentration and determining that the concentration of Troponin T from the patient is greater than the first Troponin reference concentration and less than the second Troponin reference concentration; and
   administering a treatment to treat intermittent atrial fibrillation, wherein the treatment is administration of a compound selected from the group consisting of a beta blocker, a non-dihydropyridine calcium channel blocker, digoxin, a vitamin K antagonist, acetylsalicylic acid, and a factor Xa inhibitor.

6. The method of claim 5, wherein the patient also has ischemic stroke.

7. The method of claim 6 wherein the sample is obtained immediately after the onset of symptoms of ischemic stroke.

8. The method of claim 6 wherein the sample is obtained not more than 12 hours after the onset of symptoms of ischemic stroke.

9. The method of claim 1 wherein the treatment is administration of a beta blocker.

10. The method of claim 1 wherein the treatment is administration of a non-dihydropyridine calcium channel blocker.

11. The method of claim 1 wherein the treatment is administration of digoxin.

12. The method of claim 1 wherein the treatment is administration of a vitamin K antagonist.

13. The method of claim 1 wherein the treatment is administration of acetylsalicylic acid.

14. The method of claim 1 wherein the treatment is administration of a factor Xa inhibitor.

* * * * *